United States Patent [19]

Schohe-Loop et al.

[11] Patent Number: 5,739,127
[45] Date of Patent: Apr. 14, 1998

[54] 2,4'-BRIDGED BIS-2,4-DIAMINOQUINAZOLINES

[75] Inventors: Rudolf Schohe-Loop, Wuppertal;
Peter-Rudolf Seidel, Köln; William Bullock; Gabriele Handke, both of Wuppertal; Achim Feurer, Odenthal; Wolfgang Röben, Bergisch Gladbach; Georg Terstappen, Düsseldorf; Joachim Schuhmacher, Wuppertal; Franz-Josef van der Staay, Lohmar/Wahlscheid; Bernard Schmidt, Lindlar, all of Germany; Richard J. Fanelli, Madison, Conn.; Jane C. Chisholm, Clinton, Conn.; Richard T. McCarthy, Madison, Conn.

[73] Assignee: Bayer Aktiengesellschaft, Leverkusen, Germany

[21] Appl. No.: 745,591

[22] Filed: Nov. 8, 1996

[51] Int. Cl.[6] .................... C07D 403/02; C07D 403/14; A61K 31/535; A61K 31/505
[52] U.S. Cl. .................... 514/218; 514/260; 514/254; 514/234.5; 544/284; 544/116; 544/119; 540/575
[58] Field of Search .................... 544/284, 116, 544/119; 514/260, 234.5, 218, 254; 540/575

[56] References Cited

U.S. PATENT DOCUMENTS 4,256,738  3/1981  Woitun et al. .................... 424/180
4,734,418  3/1988  Yokoyama et al. .................... 514/260

Primary Examiner—Matthew V. Grumbling
Attorney, Agent, or Firm—Sprung Kramer Schaefer & Briscoe

[57] ABSTRACT

The present invention provides 2,4'-bridged bis-2,4-diaminoquinazolines of the general formula (I):

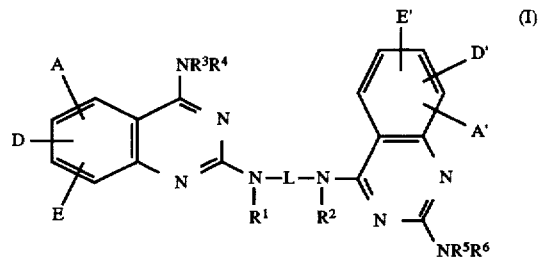

in which the indicated substituents are as defined in the description.

The invention also provides a process for the preparation of the compounds of the formula (I), drugs containing said compounds and processes for the preparation of drugs containing said compounds.

7 Claims, No Drawings

2,4'-BRIDGED BIS-2,4-DIAMINOQUINAZOLINES

The present invention relates to 2,4'-bridged bis-2,4-diaminoquinazolines, to processes for their preparation and to their use in drugs, especially as agents acting on the brain.

4,4'-Diamino-2,2'-piperazinyl-bridged, alkoxy-substituted bisquinazolines and their peripheral action, especially as antihypertensives, are known [cf. EP 188 094].

The present invention relates to 2,4'-bridged bis-2,4-diaminoquinazolines of the general formula (I):

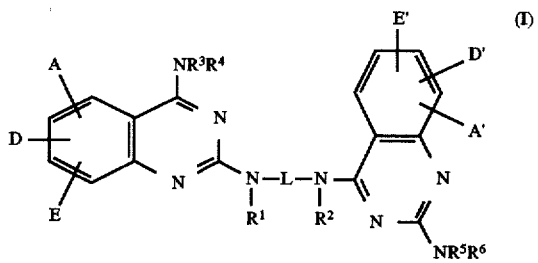

in which

A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms, L is a linear or branched alkylene chain having up to 12 carbon atoms which is optionally interrupted by an oxygen or sulfur atom or by a group of the formula —$NR^7$, wherein $R^7$ is hydrogen or linear or branched alkyl having up to 4 carbon atoms, and where the alkylene chain is optionally substituted by up to 3 identical or different substituents selected from hydroxyl, linear or branched alkoxy having up to 5 carbon atoms, aryl or aralkoxy, each of which has up to 10 carbon atoms, and a 5- to 7-membered aromatic, optionally benzo-fused heterocycle having up to 3 heteroatoms from the group comprising S, N and/or O, it being possible for the rings in turn to be substituted by halogen, hydroxyl, cyano, linear or branched alkoxy having up to 6 carbon atoms, or a radical of the formula —$(NH)_a$—$CONR^8R^9$, wherein $R^8$ and $R^9$ are identical or different and are hydrogen or linear or branched alkyl having up to 6 carbon atoms, and a is the number 0 or 1, or L is a radical of the formula —$(CH_2)_b$—T—$(CH_2)_c$, wherein b and c are identical or different and are the number 0, 1, 2, 3, 4 or 5, and T is cycloalkyl having 3 to 6 carbon atoms, aryl having 6 to 10 carbon atoms or a 3- to 8-membered, saturated or unsaturated, optionally benzo-fused and/or heterocyclically or carbocyclically bridged heterocycle having up to 3 heteroatoms from the group comprising S, N and/or O, all the ring systems optionally being substituted by up to 3 identical or different substituents selected from halogen, cyano, hydroxyl, nitro, carboxyl, linear or branched alkyl, alkoxycarbonyl or alkoxy, each of which has up to 9 carbon atoms, and a radical of the formula —CO—$NR^{10}R^{11}$, wherein and $R^{10}$ and $R^{11}$ are identical or different, are as defined above for $R^8$ and $R^9$ and are identical thereto or different therefrom, $R^1$ and $R^2$ are identical or different and are hydrogen, phenyl or linear or branched alkyl having up to 6 carbon atoms which is optionally substituted by hydroxyl, halogen or a radical of the formula —$(CO)_d$$NR^{12}R^{13}$, wherein d is the number 0 or 1 and $R^{12}$ and $R^{13}$ are identical or different, are as defined above for $R^8$ and $R^9$ and are identical thereto or different therefrom, or $R^1$, $R^2$ and L, together with the two nitrogen atoms, form a 5- to 8-membered, saturated, partially unsaturated or aromatic, optionally also benzo-fused heterocycle having up to two heteroatoms from the group comprising O, S and/or N, which is optionally substituted via a nitrogen group by hydroxyl, carboxyl, linear or branched acyl or alkoxycarbonyl, each of which has up to 6 carbon atoms, phenyl or linear or branched alkyl having up to 6 carbon atoms which in turn can be substituted by hydroxyl, carboxyl, ureido, linear or branched alkoxy, acylamino or alkoxycarbonyl, each of which has up to 5 carbon atoms, or a group of the formula —$(CO)_e$$NR^{14}R^{15}$, wherein e is the number 0 or 1 and and $R^{14}$ and $R^{15}$ are identical or different, are as defined above for $R^8$ and $R^9$ and are identical thereto or different therefrom, and/or the heterocycle is optionally substituted by a radical of the formula —$(CO)_f$—$NR^{16}R^{17}$ wherein f is as defined above for d and is identical thereto or different therefrom, and $R^{16}$ and $R^{17}$ are identical or different, are as defined above for $R^8$ and $R^9$ and are identical thereto or different therefrom, or, in the case where b is the number 0 and c is as defined above, or c is the number 0 and b is as defined above, T and $R^1$ or, respectively, T and $R^2$, in each case together with the nitrogen atom, form a 3- to 8-membered, optionally benzo-fused and/or heterocyclically or carbocyclically bridged, saturated heterocycle having up to 2 heteroatoms from the group comprising S, N and/or O, and $R^3$, $R^4$, $R^5$ and $R^6$ are identical or different and are hydrogen, phenyl, benzyl or linear or branched alkyl having up to 8 carbon atoms, both the rings and the alkyl optionally being substituted by up to 3 identical or different substituents selected from carboxyl, phenyl, hydroxyl, halogen and a radical of the formula —$(CO)_g$$NR^{18}R^{19}$, wherein f is the number 0 or 1 and $R^{18}$ and $R^{19}$ are identical or different, are as defined above for $R^8$ and $R^9$ and are identical thereto or different therefrom, or R³ and R⁴ and/or R⁵ and R⁶, in each case together with the nitrogen atom, form a radical of the formula

[structure: bicyclic ring with N—CH₃]

or a 5- to 7-membered saturated heterocycle which can optionally contain a further heteroatom from the group comprising S and O, or a radical of the formula —NR²⁰, wherein R²⁰ is hydrogen or a linear or branched alkyl chain having up to 6 carbon atoms which is optionally substituted by up to 3 identical or different substituents selected from hydroxyl, linear or branched alkoxy having up to 5 carbon atoms, halogen, cyano and a radical of the formula—(CO)$_h$NR²¹R²², wherein h is the number 0 or 1 and

R²¹ and R²² are identical or different and are hydrogen or linear or branched alkyl having up to 6 carbon atoms, or R²⁰ is cycloalkyl having 3 to 8 carbon atoms, phenyl or a radical of the formula

[structure: —H₂C— benzodioxole]

where the heterocycle is optionally substituted by up to 3 identical or different substituents selected from cycloalkyl having 3 to 6 carbon atoms, carboxyl, phenyl, linear or branched alkoxycarbonyl having up to 6 carbon atoms, and a group of the formula —CO—NR²³R²⁴, wherein R²³ and R²⁴ are identical or different, are as defined above for R⁸ and R⁹ and are identical thereto or different therefrom, and/or is optionally substituted by linear or branched alkyl having up to 6 carbon atoms which is optionally substituted by phenoxy, which in turn can be substituted by up to 3 identical or different halogens, and/or is optionally substituted by linear or branched alkoxy having up to 6 carbon atoms which in turn can be substituted by a 5- to 7-membered aromatic, optionally also benzo-fused heterocycle having up to 2 heteroatoms from the group comprising S, N and/or O, and/or their salts.

Biocompatible salts are preferred within the framework of the present invention. Biocompatible salts of the novel 2,4'-bridged bis-2,4-diaminoquinazolines can be salts of the substances according to the invention with mineral acids, carboxylic acids or sulfonic acids. Examples of particularly preferred salts are those with hydrochloric acid, hydrobromic acid, sulfuric acid, phosphoric acid, methanesulfonic acid, ethanesulfonic acid, toluenesulfonic acid, benzenes naphthalenedisulfonic acid, acetic acid, propionic acid, lactic acid, tartaric acid, citric acid, fumaric acid, maleic acid or benzoic acid.

The compounds according to the invention can be present in different stereoisomeric forms within the framework of the present invention. The compounds according to the invention exist in stereoisomeric forms which either behave as image and mirror image (enantiomers) or do not behave as image and mirror image (diastereoisomers). The invention relates both to the antipodes and to the racemic forms and the diastereoisomeric mixtures. The racemic forms and the diastereoisomers can be resolved in known manner into the stereoisomerically components.

Within the framework of the invention, a heterocycle is generally a saturated or unsaturated 5- to 8-membered, preferably 6- or 7-membered heterocycle which can contain up to 3 heteroatoms from the group comprising S, N and/or O. Examples which may be mentioned are pyridyl, thienyl, furyl, pyrrolyl, thiazolyl, oxazolyl, imidazolyl, morpholinyl or piperidyl. Pyridyl and thienyl are preferred.

A 3- to 8-membered saturated heterocycle bonded via the nitrogen atom, which can also contain up to 2 oxygen, sulfur and/or nitrogen atoms as heteroatoms, is generally azetidinyl, piperidyl, morpholinyl, piperazinyl, pyrrolidinyl, 1,4-diazacycloheptyl or [1,5]-diazoxanyl. 7- and 8-membered rings with one oxygen atom and/or up to 2 nitrogen atoms, for example 1,4-diazacycloheptyl or [1,5]-diazoxanyl, are preferred. 1,4-Diazacycloheptyl and [1,5]-diazoxanyl are particularly preferred.

Preferred compounds of the general formula (I) are those in which A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 5 carbon atoms, L is a linear or branched alkylene chain having up to 10 carbon atoms which is optionally interrupted by an oxygen or sulfur atom or by a group of the formula —NR⁷, wherein R⁷ is hydrogen or linear or branched alkyl having up to 3 carbon atoms, and where the alkylene chain is optionally substituted by up to 2 identical or different substituents selected from hydroxyl, linear or branched alkoxy having up to 4 carbon atoms, phenyl, phenoxy, pyridyl and pyrimidinyl, it being possible for the rings in turn to be substituted by fluorine, chlorine, bromine, hydroxyl, cyano, linear or branched alkoxy having up to 5 carbon atoms, or a radical of the formula —(NH)$_a$—CONR⁸R⁹, wherein R⁸ and R⁹ are identical or different and are hydrogen or linear or branched alkyl having up to 5 carbon atoms, and a is the number 0 or 1, or L is a radical of the formula —(CH₂)$_b$—T—(CH₂)$_c$, wherein b and c are identical or different and are the number 0, 1, 2, 3 or 4, and T is cyclopropyl, cyclobutyl, cyclopentyl or cyclohexyl or is phenyl, piperidinyl, pyridazinyl, pyridyl or thienyl which is optionally substituted by up to 2 identical or different substituents selected from fluorine, chlorine, bromine, cyano, hydroxyl, nitro, carboxyl, linear or branched alkyl, alkoxycarbonyl or alkoxy, each of which has up to 8 carbon atoms, and a radical of the formula —CO—NR¹⁰R¹¹, wherein R¹⁰ and R¹¹ are identical or different, are as defined above for R⁸ and R⁹ and are identical thereto or different therefrom, $R^1$ and $R^2$ are identical or different and are hydrogen, phenyl or linear or branched alkyl having up to 5 carbon atoms which is optionally substituted by hydroxyl, fluorine, chlorine, bromine or a radical of the formula —$(CO)_d NR^{12}R^{13}$, wherein d is the number 0 or 1 and $R^{12}$ and $R^{13}$ are identical or different, are as defined above for $R^8$ and $R^9$ and are identical thereto or different therefrom, or $R^1$, $R^2$ and L, together with the two nitrogen atoms, form a piperazinyl, homopiperazinyl or diazabicyclooctanyl ring which is optionally substituted via a nitrogen group by hydroxyl, carboxyl, linear or branched acyl or alkoxycarbonyl, each of which has up to 5 carbon atoms, phenyl or linear or branched alkyl having up to 5 carbon atoms which in turn can be substituted by hydroxyl, carboxyl, ureido, linear or branched alkoxy, acylamino or alkoxycarbonyl, each of which has up to 4 carbon atoms, or a group of the formula —(CO)$_e$NR$^{14}$R$^{15}$, wherein e is the number 0 or 1 and $R^{14}$ and $R^{15}$ are identical or different, are as defined above for $R^8$ and $R^9$ and are identical thereto or different therefrom, and/or the piperazinyl, homopiperazinyl or diazabicyclooctanyl ring is optionally substituted by a radical of the formula —(CO)$_f$—NR$^{16}$R$^{17}$, wherein f is as defined above for d and is identical thereto or different therefrom, and and $R^{16}$ and $R^{17}$ are identical or different, are as defined above for $R^8$ and $R^9$ and are identical thereto or different therefrom, or, in the case where b is the number 0 and c is as defined above, or c is the number 0 and b is as defined above, T and $R^1$ or, respectively, T and $R^2$, in each case together with the nitrogen atom, form a pyrrolidinyl or piperidinyl ring, ps and $R^3$, $R^4$, $R^5$ and $R^6$ are identical or different and are hydrogen, phenyl, benzyl or linear or branched alkyl having up to 7 carbon atoms, both the rings and the alkyl optionally being substituted bey up to 2 identical or different substituents selected from carboxyl, phenyl, hydroxyl, fluorine, chlorine, bromine and a radical of the formula —(CO$_g$NR$^{18}$R$^{19}$, wherein g is the number 0 or 1 and $R^{18}$ and $R^{19}$ are identical or different, are as defined above for $R^8$ and $R^9$ and are identical thereto or different therefrom, or $R^3$ and $R^4$ and/or $R^5$ and $R^6$, in each case together with the nitrogen atom, form a morpholine, pyrrolidine, piperidine or thiomorpholine ring or a radical of the formula

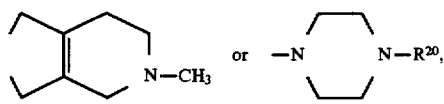

wherein $R^{20}$ is hydrogen or a linear or branched alkyl chain having up to 5 carbon atoms which is optionally substituted by up to 2 identical or different substituents selected from hydroxyl, linear or branched alkoxy having up to 4 carbon atoms, fluorine, chlorine, bromine, cyano and a radical of the formula —(CO)$_h$NR$^{21}$R$^{22}$, wherein h is the number 0 or 1 and $R^{21}$ and $R^{22}$ are identical or different and are hydrogen or linear or branched alkyl having up to 5 carbon atoms, or $R^{20}$ is cyclopropyl, cyclobutyl, cyclopentyl, cyclohexyl, phenyl or a radical of the formula

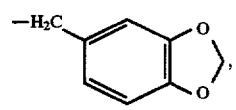

where the heterocycles listed above are optionally substituted by up to 2 identical or different substituents selected from cyclopropyl, cyclobutyl, cyclopentyl, cyclohexyl, carboxyl, phenyl, linear or branched alkyl or alkoxycarbonyl, each of which has up to 5 carbon atoms, and a group of the formula —CO—NR$^{23}$R$^{24}$, wherein $R^{23}$ and $R^{24}$ are identical or different, are as defined above for $R^8$ and $R^9$ and are identical thereto or different therefrom, and/or are optionally substituted by linear or branched alkyl having up to 5 carbon atoms which is optionally substituted by phenoxy, which in turn can be substituted by up to 2 identical or different substituents selected from fluorine, chlorine and bromine, and/or are optionally substituted by linear or branched alkoxy having up to 5 carbon atoms which in turn can be substituted by a morpholine, pyrrolidine, piperidine, thiomorpholine or piperazine ring, and/or their salts.

Particularly preferred compounds of the general formula (I) are those in which

A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 3 carbon atoms, L is a linear or branched alkylene chain having up to 8 carbon atoms which is optionally interrupted by a group of the formula —NR$^7$, wherein $R^7$ is hydrogen, methyl or ethyl, and where the alkylene chain is optionally substituted by hydroxyl, linear or branched alkoxy having up to 3 carbon atoms, phenyl, phenoxy or pyridyl, it being possible for the rings in turn to be substituted by fluorine, chlorine, bromine, hydroxyl, cyano, linear or branched alkoxy having up to 3 carbon atoms, or a radical of the formula —(NH)$_a$—CONR$^8$R$^9$, wherein R⁸ and R⁹ are identical or different and are hydrogen or linear or branched alkyl having up to 3 carbon atoms, and a is the number 0 or 1, or L is a radical of the formula —(CH₂)$_b$—T—(CH₂)$_c$, wherein b and c are identical or different and are the number 0, 1, 2 or 3, and T is cyclopropyl, cyclobutyl, cyclopentyl or cyclohexyl or is phenyl, piperidinyl, pyridazinyl, pyridyl or thienyl which is optionally substituted by up to 3 identical or different substituents selected from fluorine, chlorine, bromine, cyano, hydroxyl, nitro, carboxyl, linear or branched alkyl, alkoxycarbonyl or alkoxy, each of which has up to 6 carbon atoms, and a radical of the formula —CO—NR¹⁰R¹¹, wherein R¹⁰ and R¹¹ are identical or different, are as defined above for R⁸ and R⁹ and are identical thereto or different therefrom, R¹ and R² are identical or different and are hydrogen, phenyl or linear or branched alkyl having up to 4 carbon atoms which is optionally substituted by hydroxyl, fluorine, chlorine, bromine or a radical of the formula —(CO)$_d$NR¹²R¹³, wherein d is the number 0 or 1 and

R¹² and R¹³ are identical or different, are as defined above for R⁸ and R⁹ and are identical thereto or different therefrom, or R¹, R² and L, together with the two nitrogen atoms, form a piperazinyl, homopiperazinyl or diazabicyclooctanyl ring which is also optionally substituted via a nitrogen group by hydroxyl, carboxyl, linear or branched acyl or alkoxycarbonyl, each of which has up to 4 carbon atoms, phenyl or linear or branched alkyl having up to 3 carbon atoms which in turn can be substituted by hydroxyl, carboxyl, ureido, linear or branched alkoxy, acylamino or alkoxycarbonyl, each of which has up to 3 carbon atoms, or a group of the formula —(CO$_e$NR¹⁴R¹⁵, wherein e is the number 0 or 1 and

R¹⁴ and R¹⁵ are identical or different, are as defined above for R⁸ and R⁹ and are identical thereto or different therefrom, and/or the piperazinyl, homopiperazinyl or diazabicyclooctanyl ring is optionally substituted by a radical of the formula —(CO)$_f$—NR¹⁶R¹⁷, wherein f is as defined above for d and is identical thereto or different therefrom, and R¹⁶ and R¹⁷ are identical or different, are as defined above for R⁸ and R⁹ and are identical thereto or different therefrom, or, in the case where b is the number 0 and c is as defined above, or c is the number 0 and b is as defined above, T and R¹ or, respectively, T and R², in each case together with the nitrogen atom, form a pyrrolidinyl or piperidinyl ring, and R³, R⁴, R⁵ and R⁶ are identical or different and are hydrogen, phenyl, benzyl or linear or branched alkyl having up to 6 carbon atoms, both the rings and the alkyl optionally being substituted by up to 2 identical or different substituents selected from carboxyl, phenyl, hydroxyl, fluorine, chlorine, bromine and a radical of the formula —(CO)$_g$NR¹⁸R¹⁹, wherein g is the number 0 or 1 and

R¹⁸ and R¹⁹ are identical or different, are as defined above for R⁸ and R⁹ and are identical thereto or different therefrom, or R³ and R⁴ and/or R⁵ and R⁶, in each case together with the nitrogen atom, form a morpholinyl, pyrrolidinyl or piperidinyl ring or a radical of the formula

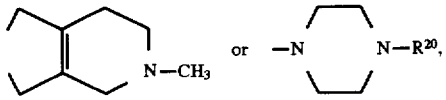

wherein

R²⁰ is hydrogen or a linear or branched alkyl chain having up to 8 carbon atoms which is optionally substituted by up to 2 identical or different substituents selected from hydroxyl, linear or branched alkoxy having up to 3 carbon atoms, fluorine, chlorine, bromine, cyano and a radical of the formula —(CO)$_h$NR²¹R²², wherein h is the number 0 or 1 and

R²¹ and R²² are identical or different and are hydrogen or linear or branched alkyl having up to 4 carbon atoms, or R²⁰ is cyclopropyl, cyclopentyl, cyclohexyl, phenyl or a radical of the formula

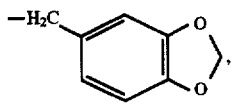

where the heterocycles listed above are optionally substituted by up to 2 identical or different substituents selected from cyclopropyl, cyclobutyl, cyclopentyl, cyclohexyl, carboxyl, phenyl, linear or branched alkyl or alkoxycarbonyl, each of which has up to 4 carbon atoms, and a group of the formula —CO—NR²³R²⁴, wherein R²³ and R²⁴ are identical or different, are as defined above for R⁸ and R⁹ and are identical thereto or different therefrom, and/or are optionally substituted by linear or branched alkyl having up to 4 carbon atoms which is optionally substituted by phenoxy, which in turn can be substituted by up to 3 identical or different substituents selected from fluorine, chlorine and bromine, and/or are optionally substituted by linear or branched alkoxy having up to 4 carbon atoms which in turn is substituted by a morpholine, pyrrolidine, piperidine, thiomorpholine or piperazine ring,
and/or their salts.

A process for the preparation of the compounds of the general formula (I) according to the invention has also been found wherein

[A] compounds of the general formula (II):

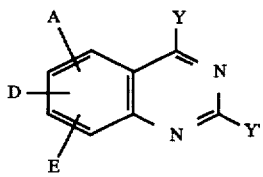
(II)

in which

A, D and E are as defined above
and

Y and Y' are identical or different and are fluorine or chlorine, are initially convened to the compounds of the general formula (IV):

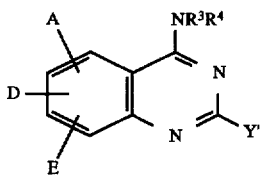
(IV)

in which

A, D, E, Y', $R^3$ and $R^4$ are as defined above, by reaction with amines of the general formula (III):

(III)

in which $R^3$ and $R^4$ are as defined above, in inert solvents, optionally in the presence of a base and/or an auxiliary, said compounds of the formula (IV) are reacted with amines of the general formula (V):

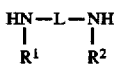
(V)

in which $R^1$, $R^2$ and L are as defined above, in inert solvents, optionally in the presence of a base and/or an auxiliary, to give the compounds of the general formula (VI):

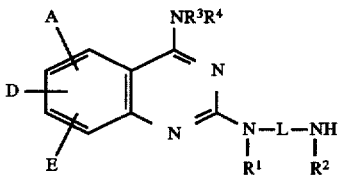
(VI)

in which

A, D, E, L, $R^1$, $R^2$, $R^3$ and $R^4$ are as defined above, said compounds of the formula (VI) are then reacted with compounds of the general formula (IIa):

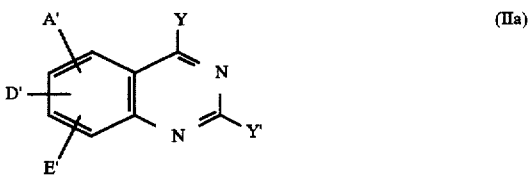
(IIa)

in which

A', D' and E' are as defined above
and

Y and Y' are identical or different and are as defined above, in inert solvents, optionally in the presence of a base, to give the compounds of the general formula (VII):

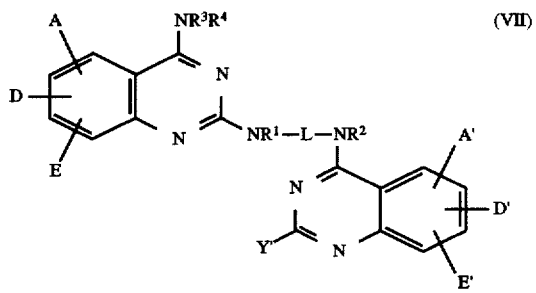
(VII)

in which

A, A', D, D', E, E', $R^1$, $R^2$, $R^3$, $R^4$, L and Y are as defined above, and, in a last step, said compounds of the formula (VII) are reacted with amines of the general formula (VIII):

(VIII)

in which $R^5$ and $R^6$ are as defined above, or

[B] compounds of the general formula (VI) are reacted with compounds of the general formula (IX):

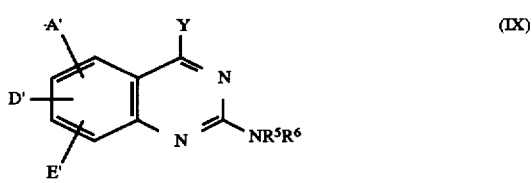
(IX)

in which

A', D', E', Y, $R^5$ and $R^6$ are as defined above, in inert solvents, optionally in the presence of a base and/or an auxiliary, or

[c] the synthesis steps indicated under [A] are carried out on a solid phase, binding to the resin being effected via the substituent radical —$NR^3R^4$ and, when the synthesis had ended, cleavage from the resin being effected by customary methods.

The process according to the invention can be exemplified by the following reaction scheme:

[A]
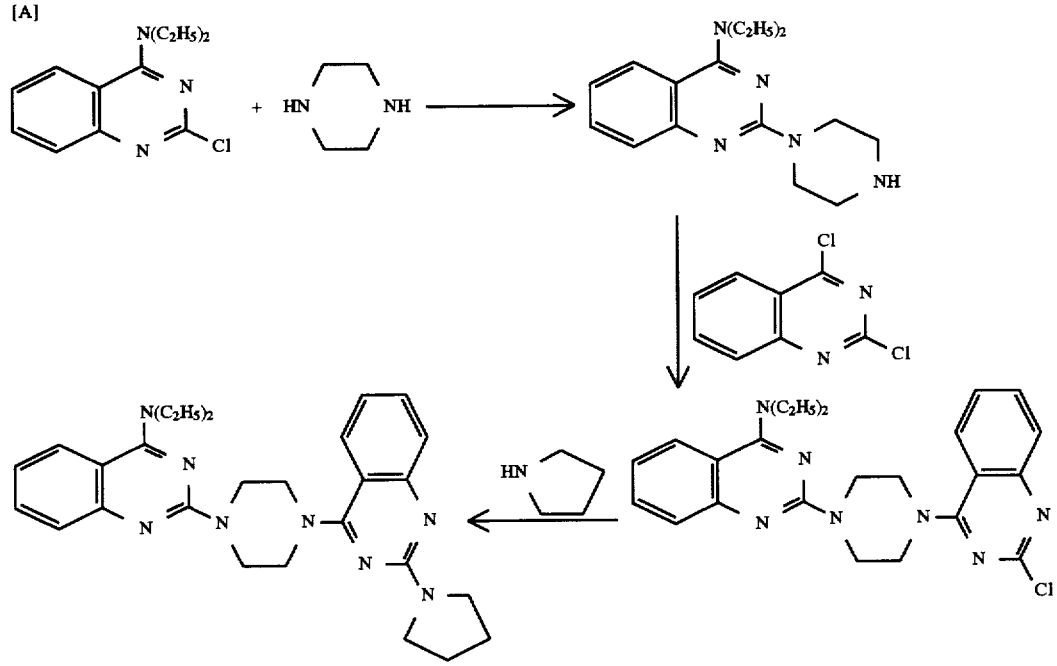
[B]
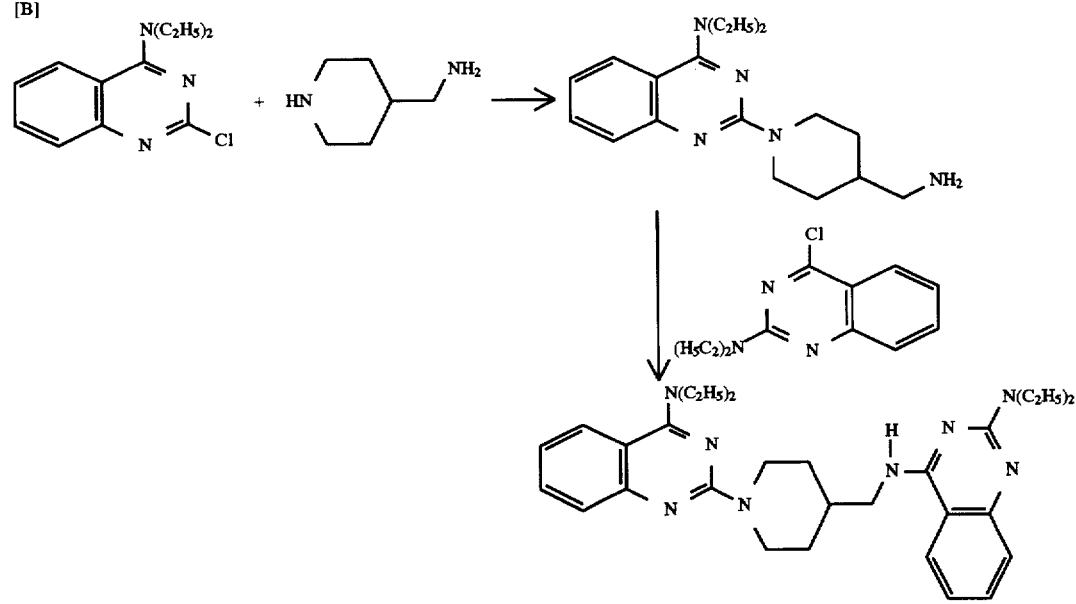

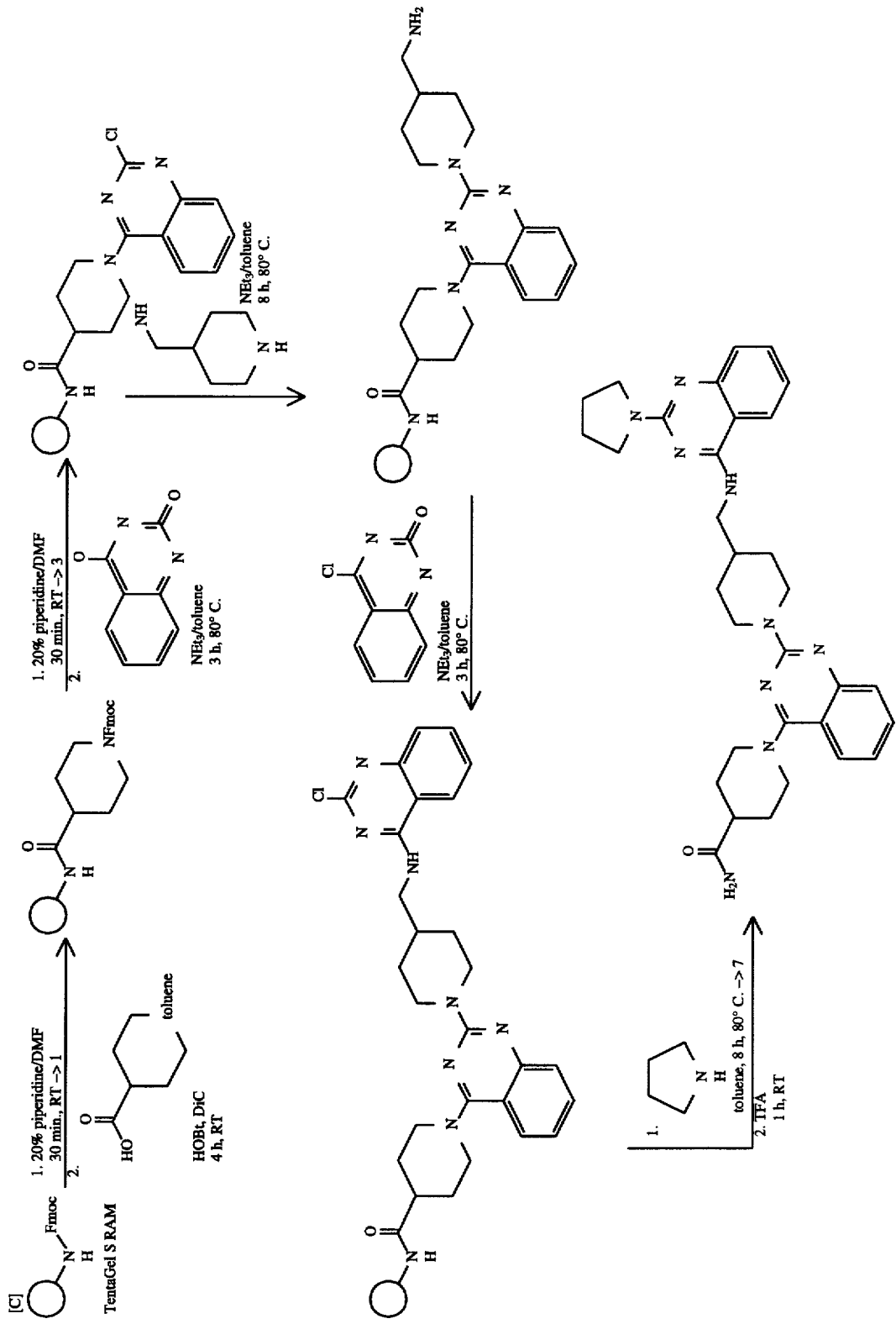

Suitable solvents are the conventional solvents which are not affected by the reaction conditions. These preferably include alcohols such as methanol, ethanol, propanol, isopropanol, hexanol, octanol or phenol, ethers such as diethyl ether, dioxane, tetrahydrofuran, glycol dimethyl ether or butyl methyl ether, ketones such as acetone or butanone, amides such as N-methylpyrrolidone, dimethylformamide or N-methylphosphorotriamide, dimethyl sulfoxide, acetonitrile, butyronitrile, ethyl acetate, halogenated hydrocarbons such as methylene chloride, chloroform or carbon tetrachloride, toluene, pyridine, picoline or N-methylpiperidine. It is also possible to use mixtures of said solvents. Toluene, tetrahydrofuran, butyronitrile, phenol and N-methylpyrrolidone are preferred. The reaction can also be carried out without a solvent.

Suitable bases are the conventional inorganic or organic bases. These preferably include alkali metal carbonates such as sodium or potassium carbonate, or organic amines such as diethylamine, triethylamine, tripropylamine, pyridine, picoline, N-methylpiperidine, lutidine or diisopropylethylamine. Diisopropylethylamine and tripropylamine are preferred.

The base is used here in an amount of 1 to 5 mol, preferably of 1 to 2 mol, based on 1 mol of the compounds of the general formulae (II), (IIa), (V) and (VIII).

Suitable auxiliaries are generally iodine salts, especially alkali metal iodides such as lithium iodide, sodium iodide, potassium iodide and cesium iodide, and tetraalkylammonium iodides such as benzyltributylammonium iodide. It is preferable to use sodium iodide and potassium iodide.

The iodine salts are generally used in an amount of 0.001 to 1 mol, based on 1 mol of the compounds of the general formulae (II), (IIa), (V) and (VIII).

Suitable solvents for process [C] are those listed above, toluene, dimethylformamide and dimethyl sulfoxide being preferred.

The reactions are generally carried out in the temperature range between −20° C. and the reflux temperature of the solvent, preferably between +20° C. and the reflux temperature of the solvent.

Process [C] is generally carried out at normal pressure and in the temperature range between +20° C. and the reflux temperature of the solvent.

The reaction can be carried out at normal, elevated or reduced pressure (e.g. 0.5 to 5 bar). It is generally carried out at normal pressure.

The solid phases which can be used for process [C] are all those which are compatible with the reaction conditions, including glass, latex, crosslinked polystyrene and similar polymers and resins. Resins and polymers, such as polystyrene resins and copolymers based on polystyrene/polyoxyethylene, are preferred. The resins used are functionalized with linkers such as Rink amide linkers [cf. H. Rink, Tetrahedron Letters, 28, 3787 (1976)], trityl chloride linkers [cf. C. C. Leznoff, Acc. Chem. Res., 11,327 (1978)], Merrifield linkers [cf. M. Bodansky et al., Peptide Synthesis, Academic Press, 2nd edition, New York (1976)], Rink amide MBHA linkers [cf. H. Rink, op. cit.], Wang linkers [of. S. -W. Wang, J. Am. Chem. Soc., 95, 1328 (1973)] or 4-hydroxymethyl-3-methoxy-phenoxy-acetic acid linkers. Rink amide linker resins are particularly preferred.

The compounds bound to the resin are generally reacted with 1–10 mol equivalents of the compounds of the formulae (II), (IIa), (V) and (VIII), based on the compound already bound to the resin. It is preferable to use 2–6 mol equivalents of the compounds of the formulae (II), (IIa) and (VIII). The compounds of the formulae (V) and (VIII) can also advantageously be used in larger excess.

Some of the compounds of the general formulae (II) and (IIa) are known or they can be prepared by known methods, for example by refluxing the corresponding 1H,3H-quinazoline-2,4-diones with phosphorus oxychloride.

Some of the compounds of the general formula (IX) are known or they can be prepared by known methods, for example by refluxing the corresponding 1H,3H-quinazoline-2,4-diones with phosphorus oxychloride in the presence of triethylamine.

The compounds of the general formulae (III), (V) and (VIII) are known per se or can be prepared by conventional methods.

Some of the compounds of the general formula (IV) are known or they can be prepared as described above.

Some of the compounds of the general formulae (VI) and (VII) are known or they can be prepared for example as described above.

The compounds according to the invention possess a valuable pharmacological spectrum of action which could not be anticipated.

The compounds according to the invention are ligands for apamine-sensitive potassium channels. This can be shown by studying the affinity for apamine binding sites, e.g. in bovine cerebral membranes. The compounds according to the invention inhibit the ion flows through these channels, as can be shown by rubidium efflux experiments and with electrophysiological methods.

The compounds have a positive influence on learning and memory faculties, as demonstrated by their performance-enhancing action in typical learning and memory models like the water maze, the Morris maze, passive avoidance or reminiscence tests in automated Skinner boxes. They possess an antidepressant potential, as verified by their activity in the Porsolt rat swimming test.

The compounds according to the invention are also suitable for the treatment of myotonic dystrophy, alcoholism and other addiction diseases, sleep disturbances and bronchial asthma.

By virtue of their pharmacological properties, the compounds according to the invention can be used for the preparation of drugs for the treatment of degenerative diseases of the central nervous system, e.g. those occurring in cases of dementia (multi-infarct dementia, MID, primary degenerative dementia, PDD, presenile Alzheimer's disease, HIV dementia and other forms of dementia).

They are also suitable for the treatment of age-related cerebral faculty impairment, organic brain syndrome (OBS) and age-associated memory impairment (AAMI).

They are suitable for the treatment of depression.

1) Binding of $^{125}$I-apamine to bovine cerebral membrane

Calf brains were obtained from the local abattoir. The hippocampus was prepared on ice and a membrane suspension was made up by homogenization twice in buffer (100 mM Tris-HCl, KCl 5 mM, pH 7.4) and centrifugation at 43,000×g. In a total volume of 500 μl, the incubation mixture contained 200 μg of membrane protein, 30 pM $^{125}$I-apamine and test substances in the concentration range $1\times10^{-9}$ to $1\times10^{-4}$M. The non-specific binding of $^{125}$I-apamine was determined in the presence of $1\times10^{-7}$M unlabelled apamine.

After preincubation for 30 rain at room temperature (test substances and membrane homogenate), the samples were placed on ice for 10 min before the radioligand was added. The main incubation time was 60 min on ice. When the reaction time had elapsed, an excess of ice-cooled incubation buffer was added to each sample and the mixture was filtered with suction through cellulose acetate/nitrate membrane filters. The amount of bound $^{125}$I-apamine was measured with a gamma counter.

TABLE A

| Ex. no. | $K_i$ |
|---|---|
| 5 | 150 nM |

2) Non-radioactive Rb$^+$efflux assay for the identification of potassium channel modulators The potassium in PC12 cells is exchanged with rubidium, which is not present in the cells. This exchange is performed by incubating the cells over a period of 4 h in a physiological buffer containing 5.4 mM RbCl without KCl. This rubidium subsequently serves as a tracer for potassium. The cells laden with Rb$^+$ in this way are washed three times and then stimulated by depolarization with 50 mM KCl to open potassium channels (10 min), causing Rb$^+$ to flow out of the cells into the supernatant according to the concentration gradient.

The rubidium contents in the cell supernatant and in the residual cells after they have been lyzed with 1% Triton X-100 are then determined by means of atomic absorption spectroscopy. The relative proportion of rubidium in the cell supernatant (=Rb$^+$ efflux) is used as a measure of the potassium channel activity.

The effect of substances on the channel activity is measured by coincubating the test substance over the ten-minute stimulation period and determining its effect on the Rb$^+$ efflux in the manner described above.

3) Morris maze

Male ICR mice, 6–8 wks old and approx. 22–28 g, were obtained from Harlan Sprague-Dawley, Inc. (Indianapolis, Ind.) and housed 8/cage with ad libitum access to food and water.

The behavioral apparatus consisted of a circular galvanized steel tank painted white with a diameter of 76 cm and divided into four equally spaced quadrants, each containing a plastic fitting that allowed for the placement of an escape platform. Prior to the start of the behavioral testing, the maze was filled daily to a depth of 1 cm above the escape platform (22 cm deep), maintained at a temperature of approx. 22° C., and was made opaque by the addition of 0.9 kg of powdered milk. Numerous stationary visual cues were present in the testing room. The data were recorded with the Multiple Zone Distance Traveled program of the Video-V analysis system (Columbus Instruments International Corp., Columbus, Ohio.). After a 1 week acclimatization to the animal facility, the mice were given a 90 sec free swim, during which no escape platform was present. One to three days later, acquisition training began and consisted of 4 trials on each day for a total of three days (12 total trials), during which no drugs were given. The mice were randomly assigned a goal quadrant in which the escape platform was located. Animals were then placed in the maze (facing away from the center) at one of four equally spaced positions around the perimeter of the maze. The starting position varied for each mouse until they had started from each of the four positions once daily. On each of the training trials, the mice were allowed 120 sec to find the goal platform. If they failed to do so within the allotted time, they were placed on the platform. The intertrial interval was 30 sec, during which time the mouse remained on the platform.

On the fourth day, the mice were given a single 30 sec probe trial in which no escape platform was present. Thirty min or 1 hr prior to the start of the probe trial, mice were randomly assigned to groups that were given either drug or vehicle, and the time spent in each quadrant was measured.

The present invention also includes pharmaceutical formulations which contain one or more compounds of the general formula (I) together with inert, non-toxic, pharmaceutically appropriate adjuncts and excipients, or which consist of one or more active substances of the formula (I), as well as processes for the preparation of these formulations.

The active substances of the formula (I) should be present in these formulations in a concentration of 0.1 to 99.5% by weight, preferably of 0.5 to 95% by weight of the total mixture.

In addition to the active substances of the formula (I), the pharmaceutical formulations can also contain other pharmaceutical active substances.

The pharmaceutical formulations mentioned above can be prepared in conventional manner by known methods, for example with one or more adjuncts or excipients.

To achieve the desired result, it has generally proved advantageous to administer the active substance or substances of the formula (I) in total mounts of about 0.01 to about 100 mg/kg, preferably in total amounts of about 0.01 mg/kg to 10 mg/kg of body weight per 24 hours, optionally in the form of several individual doses.

However, it may be advantageous to deviate from said amounts, depending on the nature and body weight of the subject treated, the individual response to the drug, the nature and severity of the disease, the type of formulation and administration and the time or interval at which the drug is administered.

Starting compounds

EXAMPLE I

2-Chloro-4-diethylaminoquinazoline

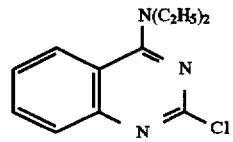

10.4 ml of diethylamine in 10 ml of diethyl ether were added dropwise to a solution of 10.0 g of 2,4-dichloroquinazoline in 400 ml of diethyl ether and the mixture was stirred for 3 h at room temperature. After distillation of the solvent under vacuum, the residue was taken up with 200 ml of methanol and stirred with 10 g of basic ion exchanger (®Lewatit M600) for 3 h. The ion exchanger was filtered off and the filtrate was concentrated to dryness on a rotary evaporator. The residue was taken up with 200 ml of dichloromethane and the solution was washed with twice 50 ml of water. After the organic phase had been dried over magnesium sulfate and the solvent stripped off, the crude product was treated with 50 ml of diethyl ether/petroleum ether (1/1) and left to crystallize at 4° C. overnight.

Yield: 9.12 g (77%)

M.p.: 76° C.

4-(1-Pyrrolidino)-2-chloroquinazoline was obtained by the same method with pyrrolidine.

The 2,4-dichloroquinazoline used as educt was prepared by known processes [Eur. J. Med. Chem. 12, 1977, 325].

2,6-Dichloro-4-diethylaminoquinazoline was prepared from 2,4,6-trichloroquinazoline by the process indicated above.

EXAMPLE II

4-Chloro-2-diethylaminoquinazoline

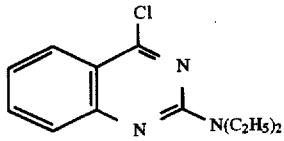

20.0 g of 1H,3H-quinazoline-2,4-dione were dissolved in 280 ml of phosphorus oxychloride, and 60 ml of triethylamine were added. After refluxing for 75 minutes, the excess phosphorus oxychloride was distilled off under vacuum and the residue was slowly introduced into 200 ml of ice-cold 1N sodium hydroxide solution. Extraction with dichloromethane (three times 150 ml), washing of the organic phase with water (three times 100 ml), drying over magnesium sulfate and distillation of the solvent on a rotary evaporator gave a brown oil, which could be used in the next reaction without further purification. Yield: 17.7 g (60%)

EXAMPLE III

4-Aminomethyl-N-(4-diethylaminoquinazolin-2-yl)-piperidine

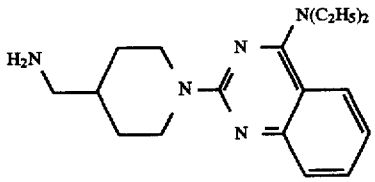

A mixture of 4-(aminomethyl)-piperidine (1.2 g, 11 mmol), 2-chloro-4-diethylaminoquinazoline (2.5 g, 11 mmol) and Hünig's base (2.8 ml, 16 mmol) in 5 ml of butyronitrile was reacted for 12 hours at 100° C. After cooling, ethyl acetate (50 ml) and 50 ml of sodium hydroxide (10%) were added. The phases were separated and the aqueous phase was extracted with ethyl acetate (2×25 ml). The combined organic phases were dried ($Na_2SO_4$), concentrated on a rotary evaporator and purified by chromatography on silica gel (eluent: methylene chloride/ethanol/ammonia, 50/10/1) to give the free base as a thick orange-brown oil.

Yield: 1.3 g (37%)

EXAMPLE IV

4-Aminomethyl-N-(2-diethylaminoquinazolin-4-yl)-piperidine

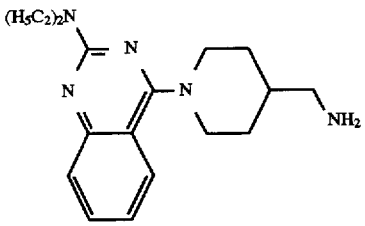

A mixture of 4-(aminomethyl)-piperidine (1.2 g, 11 mmol), 4-chloro-2-diethylaminoquinazoline (1.2 g, 5.1 mmol) and Hünig's base (2.8 ml, 16 mmol) in 10 ml of butyronitrile was reacted for 12 hours at 100° C. After cooling, ethyl acetate (50 ml) and 50 ml of sodium hydroxide (10%) were added. The phases were separated and the aqueous phase was extracted with ethyl acetate (2×25 ml). The combined organic phases were dried ($Na_2SO_4$), concentrated on a rotary evaporator and purified by chromatography on silica gel (eluent: methylene chloride/ethanol/ammonia, 50/10/1) to give the free base as a solid.

M.p.: 78° C.

Yield: 884 mg (27%)

General instructions for the preparation of 2,4'-bridged bisquinazolines on a solid phase with compounds of the general formula (III) ($HNR^3R^4$=amino acid)

a) Elimination of Fmoc (product: resin (I))

1.00 g of TentaGel S RAM (loading: 0.23 mmol/g) is shaken for 0.5 h at RT in 10 ml of a 20% solution of piperidine in DMF. The solution is then filtered with suction and the resin is washed with 6×5 ml of DMF.

b) Amino acid coupling (product: resin (2))

The resin (1) is suspended in 10 ml of DMF, treated with 0.46 mmol of an Fmoc-protected amino acid, 0.92 mmol of N,N-diisopropylcarbodiimide and 0.92 mmol of N-hydroxybenzotriazole ($xH_2O$) and shaken for 4 h at RT. The solution is then filtered with suction and the resin is washed 3 times with 5 ml each of DMF, methanol and ether. The resin is shaken for 0.5 h at RT in 10 ml of a 20% solution of piperidine in DMF. The solution is then filtered with suction and the resin is washed 3 times with 5 ml each of DMF and toluene.

c) Elimination of Fmoc (product: resin (3))

The resin (2) is shaken for 0.5 h at RT in 10 ml of a 20% solution of piperidine in DMF. The solution is then filtered with suction and the resin (3) is washed 3 times with 5 ml each of DMF and toluene.

d) Reaction with 2,4-dichloroquinazoline (product: resin (4))

The resin (3) is heated for 3 h at 80° C in 10 ml of toluene with 0.46 mmol of 2,4-dichloroquinazoline and 0.46 mmol of triethylamine, with stirring. The solution is filtered with suction and the resin (4) is washed 3 times with 5 ml each of DMF and toluene.

e) Reaction with homopiperazine or aminomethylpiperidine (product: resin (5))

The resin (4) is heated for 8 h at 80° C. in 10 ml of toluene with 0.92 mmol of homopiperazine or aminomethylpiperidine and 0.92 mmol of triethylamine, with stirring. The solution is filtered with suction and the resin (5) is washed 3 times with 5 ml each of DMF and toluene.

f) Reaction with 2,4-dichloroquinazoline (product: resin (6))

The resin (5) is heated for 3 h at 80° C. in 10 ml of toluene with 0.46 mmol of 2,4-dichloroquinazoline and 0.46 mmol of triethylamine, with stirring. The solution is filtered with suction and the resin (6) is washed 3 times with 5 ml each of DMF and toluene.

g) Reaction with secondary amine (product: resin (7))

The resin (6) is heated for 8 h at 80° C. in 10 ml of secondary amine/toluene (1/1), with stirring. The solution is filtered with suction and the resin (7) is washed 3 times with 5 ml each of toluene, DMF and methylene chloride.

h) Cleavage of the compound from the resin (product: 2,4'-bridged bisquinazolines):

The resin (7) is shaken for 1 h at RT in 10 ml of a 50% solution of trifluoroacetic acid in methylene chloride. The solution is then filtered with suction and collected. The resin is subsequently washed with 3×5 ml of methylene chloride and the combined filtrates are concentrated. Toluene is added to the residue and the solution is concentrated again. The product is purified by chromatography on silica gel (50 ml each of methylene chloride/methanol 20/1, 10/1, 7/1, 5/1, 4/1, 3/1).

DMF=dimethylformamide 2,4'-Bridged bisquinazolines of the following genetic structure were prepared according to the general instructions:

TABLE 1

| Ex. No. | Z | $R^{26}$ | $R^{25}$ | MS (ESI) |
|---|---|---|---|---|
| 1 | -N-piperidinyl-CH₂-NH- | pyrrolidin-1-yl | H₂N-C(O)-piperidin-4-yl-CH₂-N< | 566 (M + H), 283 |
| 2 | -N-piperidinyl-CH₂-NH- | piperidin-1-yl | H₂N-C(O)-piperidin-4-yl-CH₂-N< | 580 (M + H), 290 |
| 3 | -N-piperidinyl-CH₂-NH- | 4-methylpiperidin-1-yl | H₂N-C(O)-piperidin-4-yl-CH₂-N< | 594 (M + H), 297 |
| 4 | -N-piperidinyl-CH₂-NH- | 4-phenylpiperazin-1-yl | H₂N-C(O)-piperidin-4-yl-CH₂-N< | 657 (M + H), 329 |
| 5 | -N-piperidinyl-CH₂-NH- | pyrrolidin-1-yl | H₂N-C(O)-piperidin-3-yl-CH₂-N< | 566 (M + H), 283 |
| 6 | -N-piperidinyl-CH₂-NH- | piperidin-1-yl | H₂N-C(O)-piperidin-3-yl-CH₂-N< | 580 (M + H), 290 |
| 7 | -N-piperidinyl-CH₂-NH- | 4-methylpiperidin-1-yl | H₂N-C(O)-piperidin-3-yl-CH₂-N< | 594 (M + H), 297 |

TABLE 1-continued
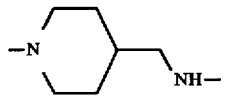
| Ex. No. | Z | R26 | R25 | MS (ESI) |
|---|---|---|---|---|
| 8 | [1-methylpiperidin-4-yl]methyl-NH— | morpholine (N-linked) | 1-methylpiperidin-3-yl-C(O)NH2 | 582 (M + H), 291 |
| 9 | piperazine (N,N'-linked) | piperidine (N-linked) | 4-(H2N-C(O))-benzyl-NH— | 588 (M + H), 294 |
| 10 | piperazine (N,N'-linked) | 4-methylpiperidine (N-linked) | 4-(H2N-C(O))-benzyl-NH— | 602 (M + H), 301 |
TABLE 2
| Ex.-No. | Structure | MS (ESI) |
|---|---|---|
| 11 | 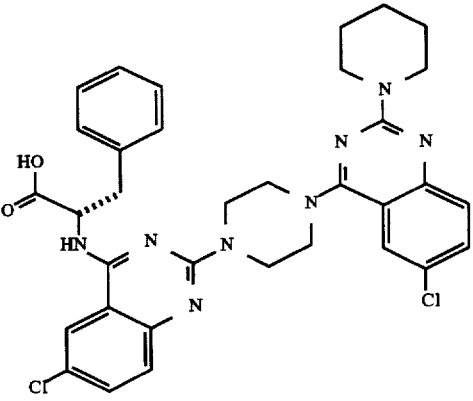 | 657 (M + H) |

TABLE 2-continued

| Ex.-No. | Structure | MS (ESI) |
|---|---|---|
| 12 | 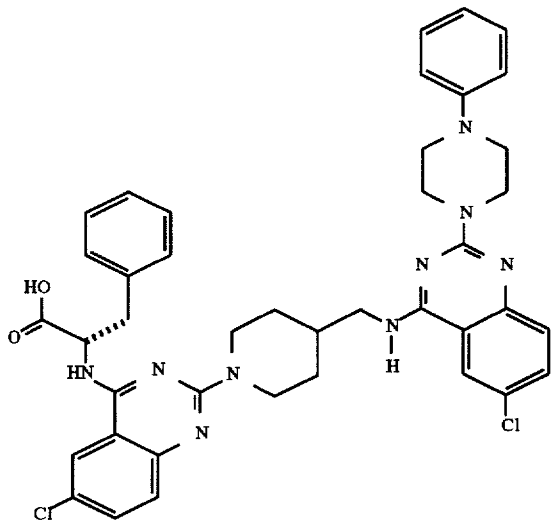 | 762 (M + H) |
| 13 | 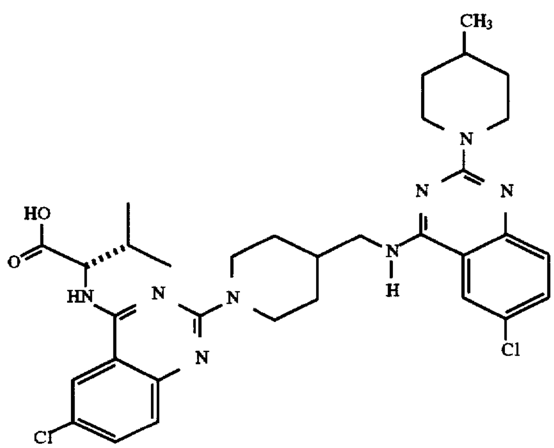 | 651 (M + H) |
| 14 | 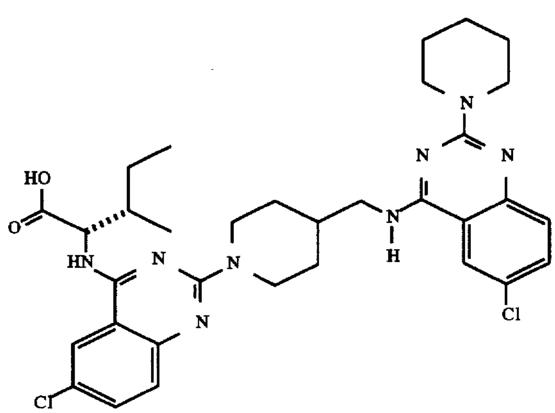 | 651 (M + H) |

TABLE 2-continued

| Ex.-No. | Structure | MS (ESI) |
|---|---|---|
| 15 | 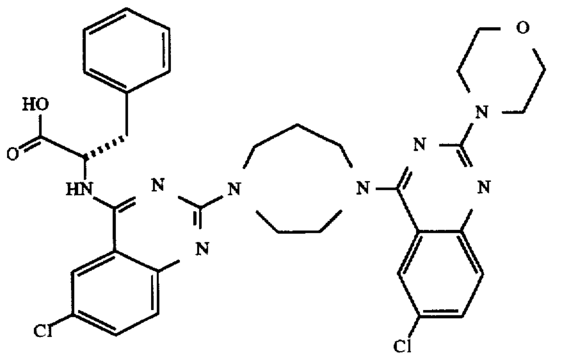 | 673 (M + H) |
| 16 | 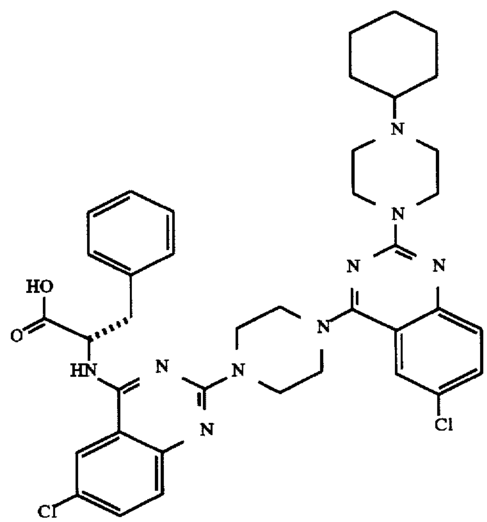 | 740 (M + H) |
| 17 | 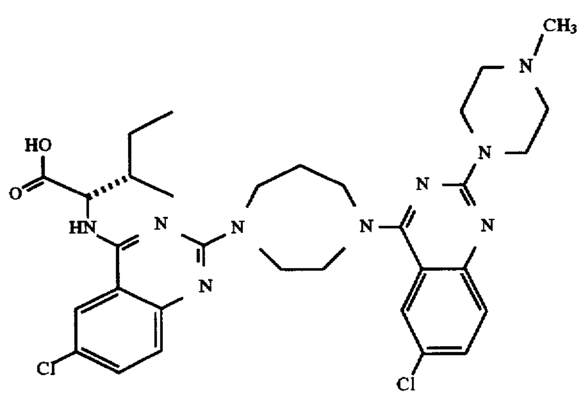 | 652 (M + H) |

TABLE 2-continued
| Ex.-No. | Structure | MS (ESI) |
|---|---|---|
| 18 | 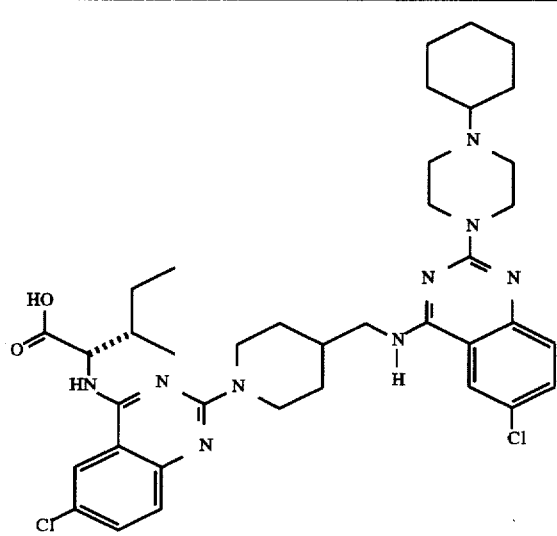 | 734 (M + H) |
| 19 | 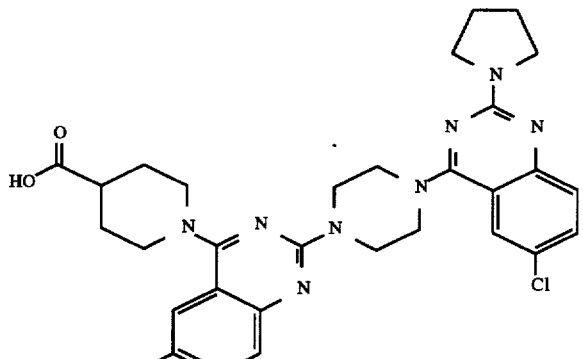 | 607 (M + H) |
| 20 | 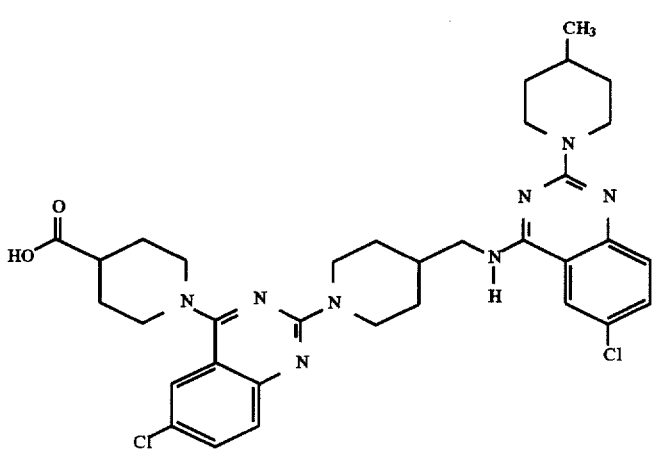 | 663 (M + H) |

TABLE 2-continued
| Ex.-No. | Structure | MS (ESI) |
|---|---|---|
| 21 | 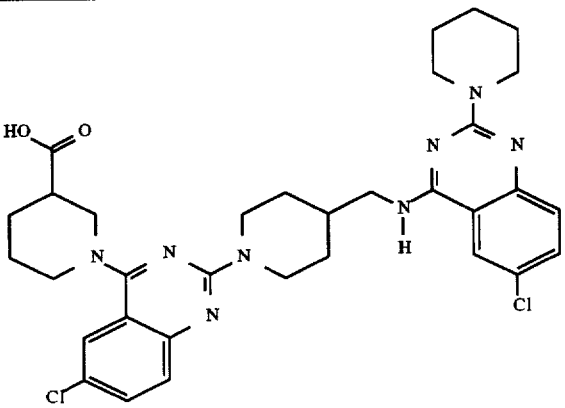 | 649 (M + H) |
| 22 | 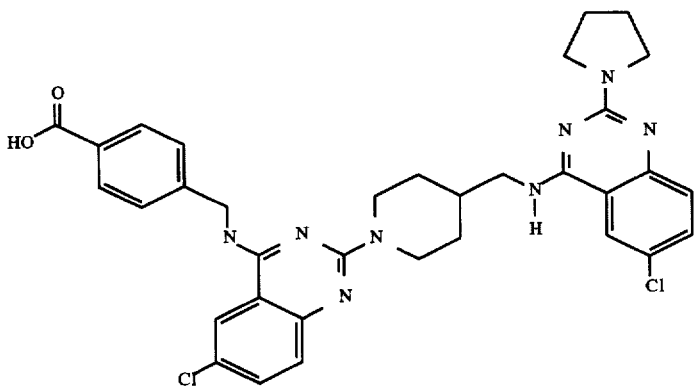 | 657 (M + H) |
| 23 | 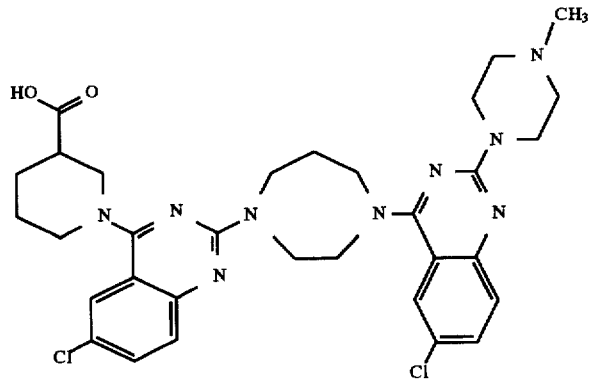 | 650 (M + H) |
| 24 | 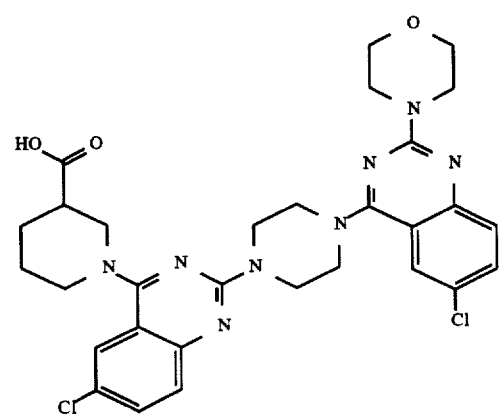 | 623 (M + H) |

TABLE 2-continued

| Ex.-No. | Structure | MS (ESI) |
|---|---|---|
| 25 | 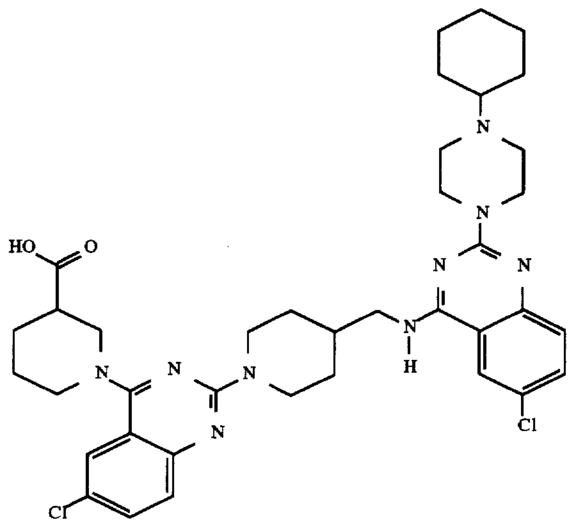 | 732 (M + H) |
| 26 | 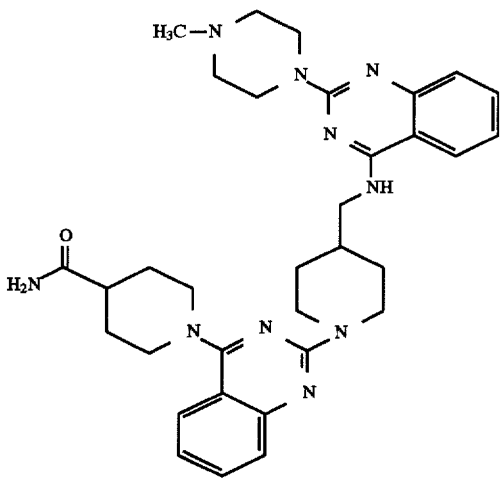 | 595 (M + H) |
| 27 | 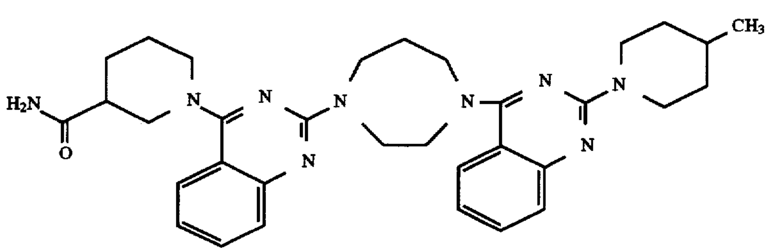 | 580 (M + H) |
| 28 | 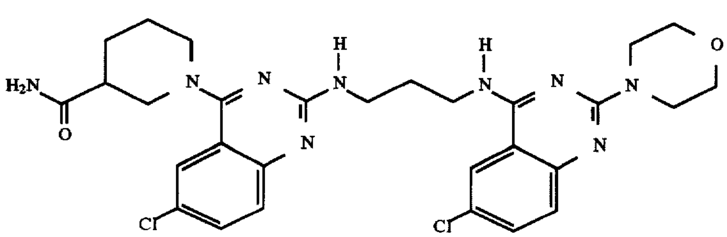 | 610 (M + H) |

TABLE 2-continued

| Ex.-No. | Structure | MS (ESI) |
|---|---|---|
| 29 | 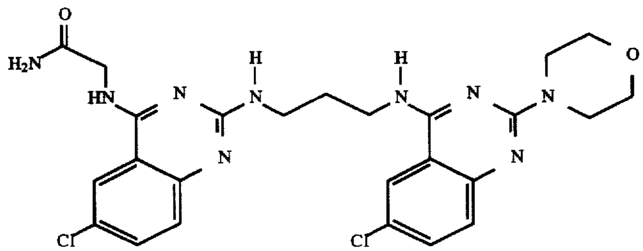 | 556 (M + H) |
| 30 | 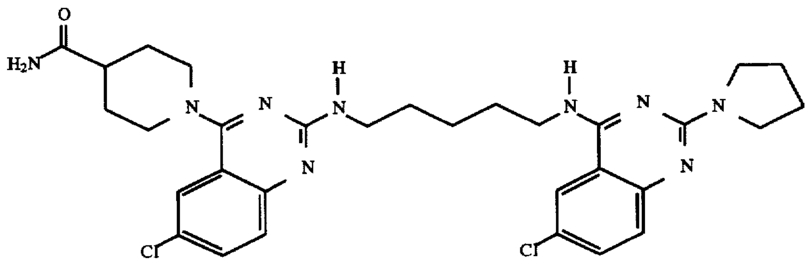 | 622 (M + H) |
| 31 | 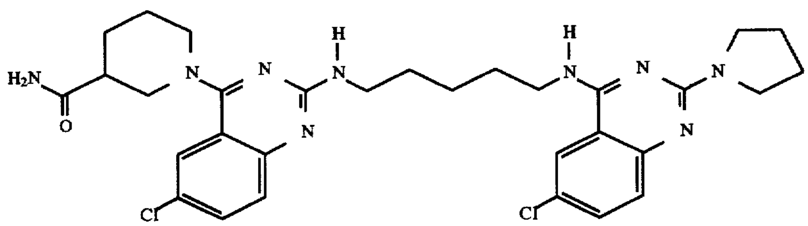 | 622 (M + H) |
| 32 | 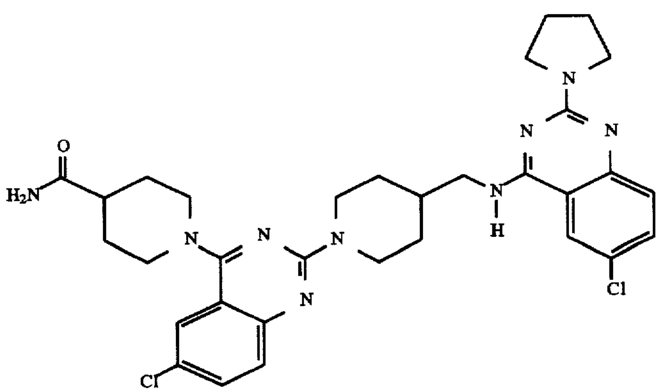 | 634 (M + H) |
| 33 | 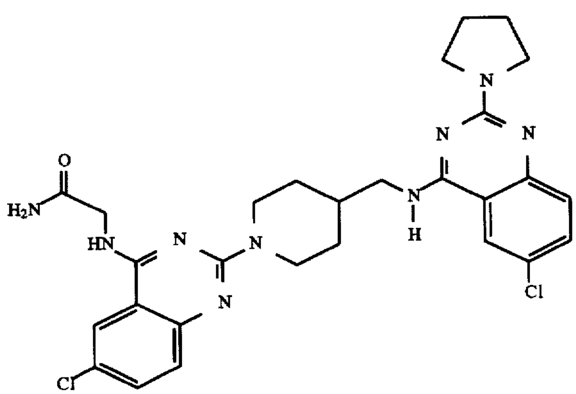 | 580 (M + H) |

TABLE 2-continued

| Ex.-No. | Structure | MS (ESI) |
|---|---|---|
| 34 | 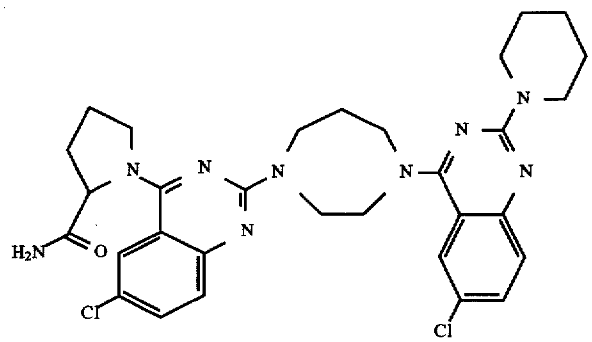 | 620 (M + H) |
| 35 | 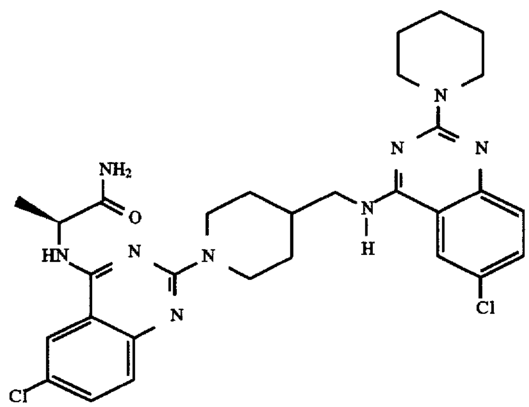 | 608 (M + H) |
| 36 | 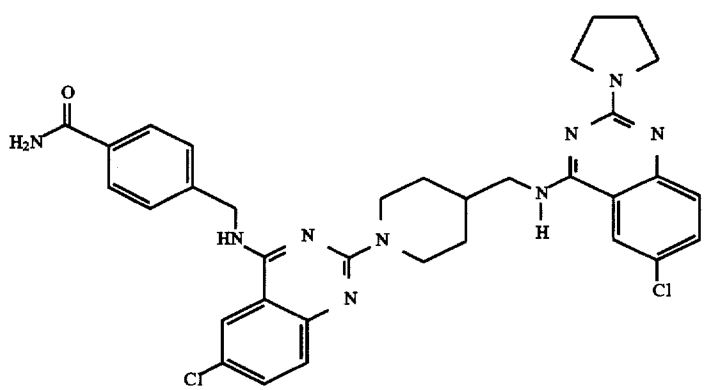 | 656 (M + H) |

TABLE 2-continued

| Ex.-No. | Structure | MS (ESI) |
|---|---|---|
| 37 | 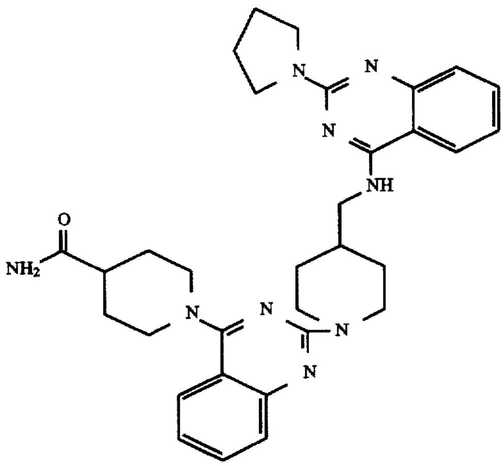 | |
| 38 | 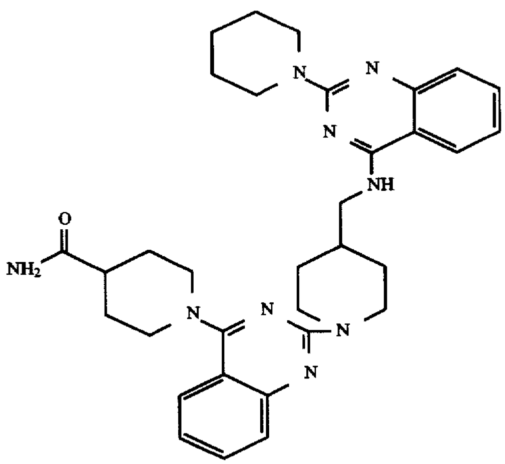 | |
| 39 | 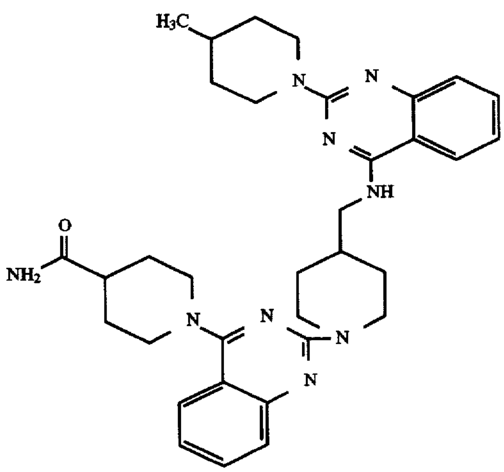 | |

TABLE 2-continued
| Ex.-No. | Structure | MS (ESI) |
| --- | --- | --- |
| 40 | 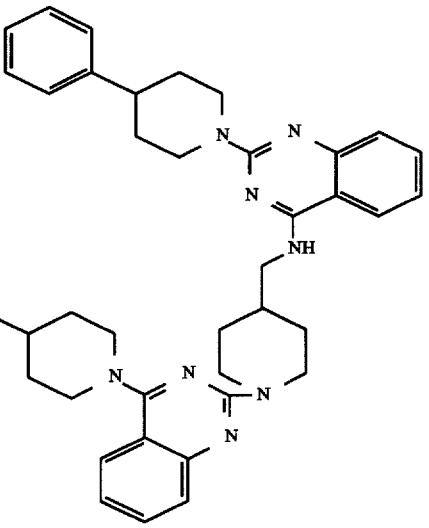 | |
| 41 | 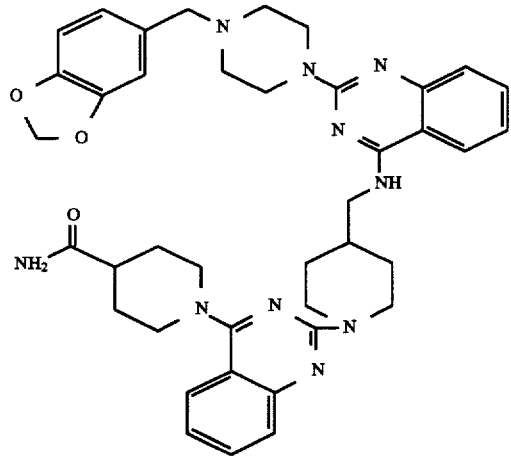 | |
| 42 | 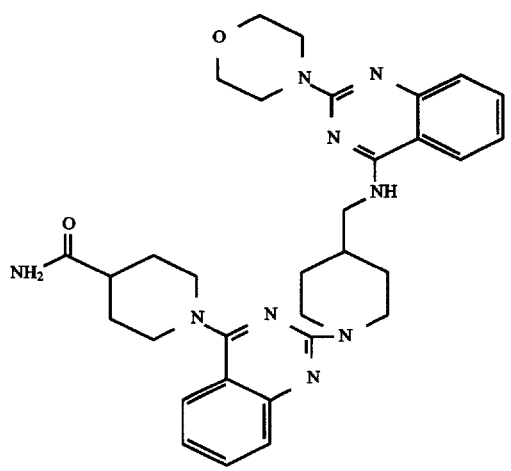 | |

TABLE 2-continued

| Ex.-No. | Structure | MS (ESI) |
|---|---|---|
| 43 | 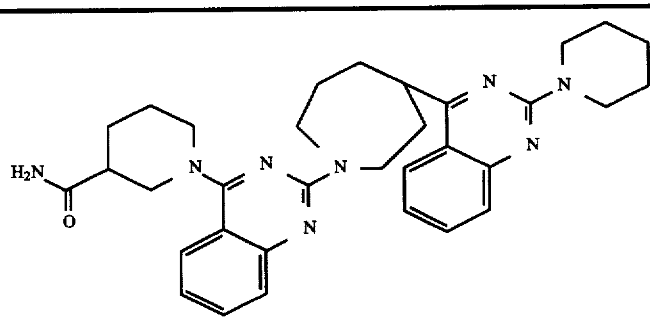 | |
| 44 | 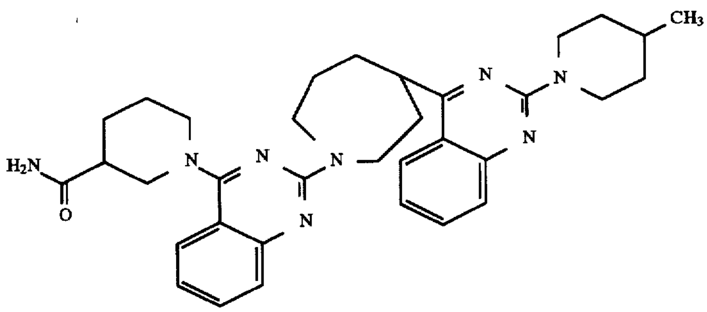 | |
| 45 | 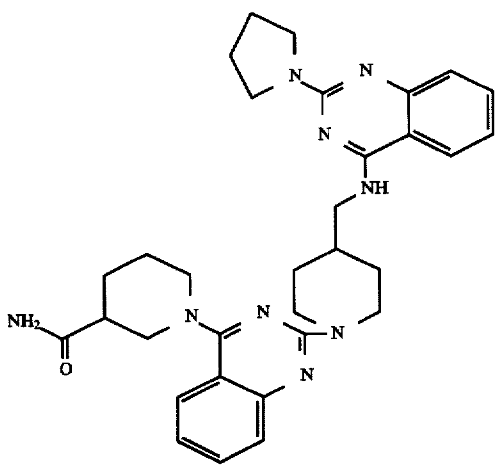 | |
| 46 | 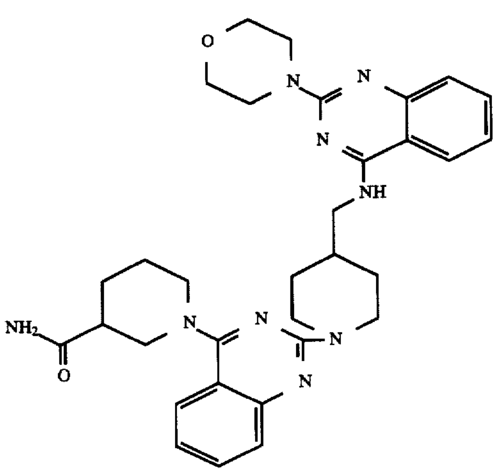 | |

TABLE 2-continued

| Ex.-No. | Structure | MS (ESI) |
|---|---|---|
| 47 | 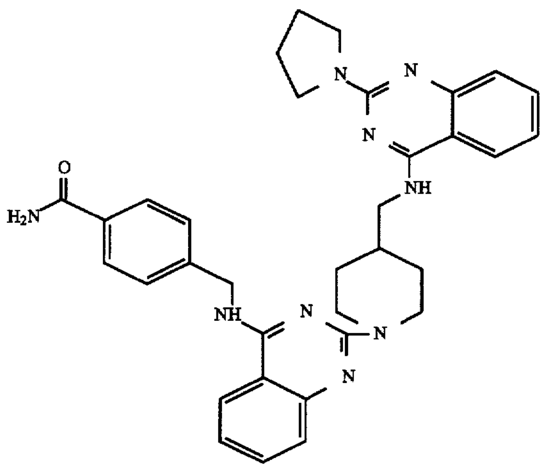 | |
| 48 | 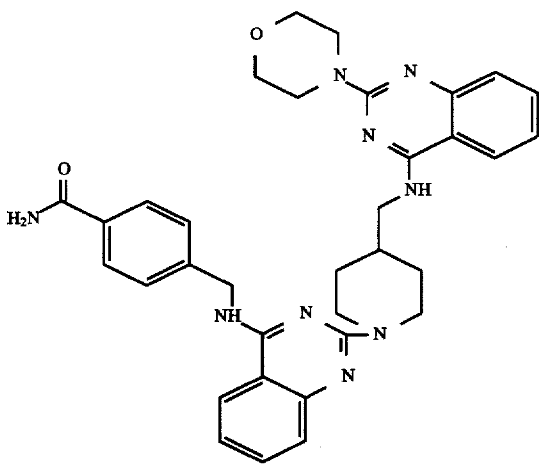 | |
| 49 | 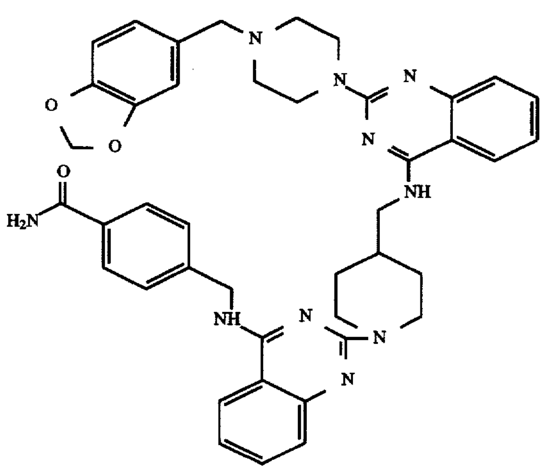 | |

TABLE 2-continued

| Ex.-No. | Structure | MS (ESI) |
|---|---|---|
| 50 | 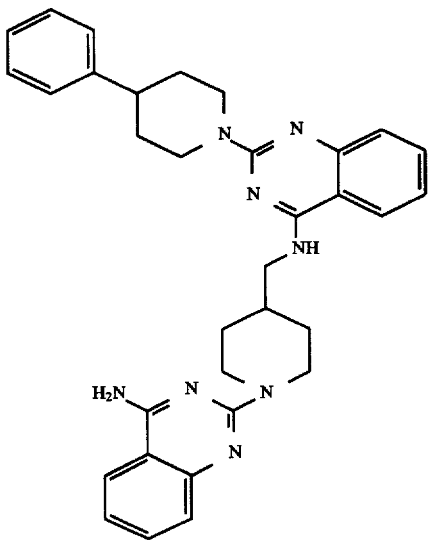 | |
| 51 | 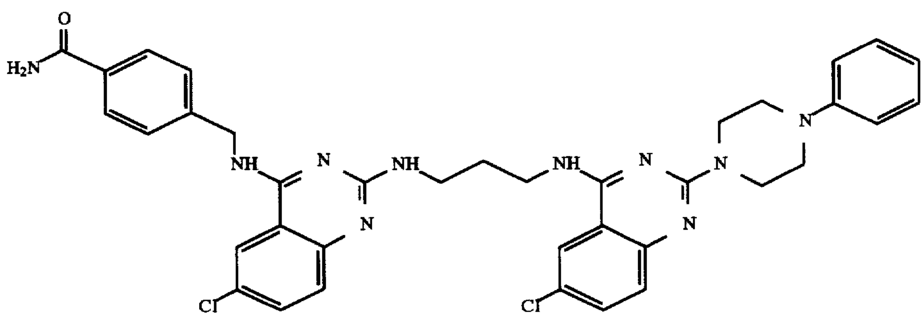 | |
| 52 | 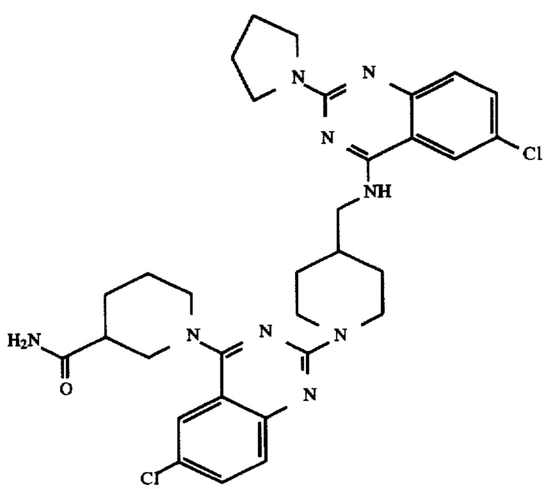 | |

TABLE 2-continued

| Ex.-No. | Structure | MS (ESI) |
|---|---|---|
| 53 | 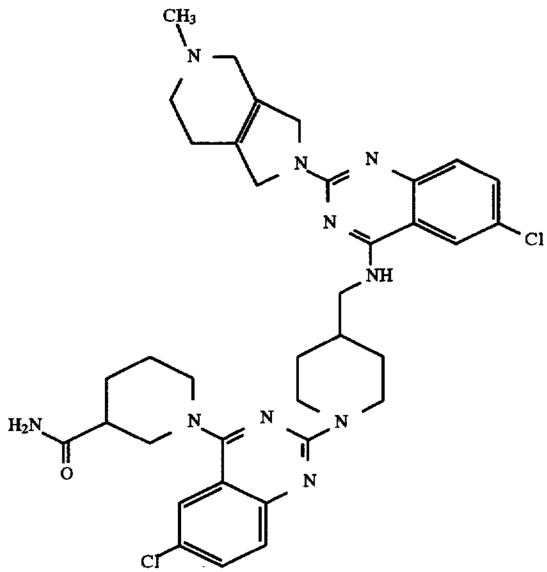 | |
| 54 | 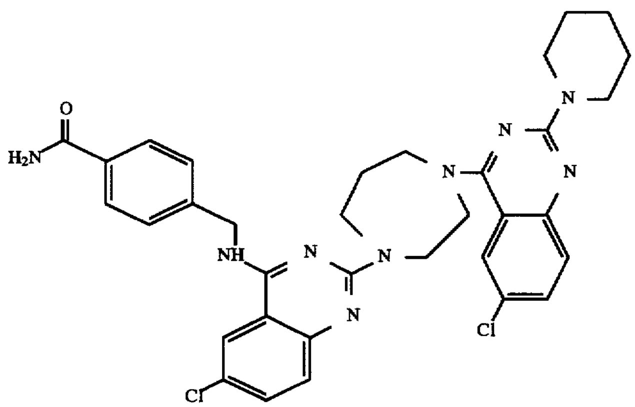 | |
| 55 | 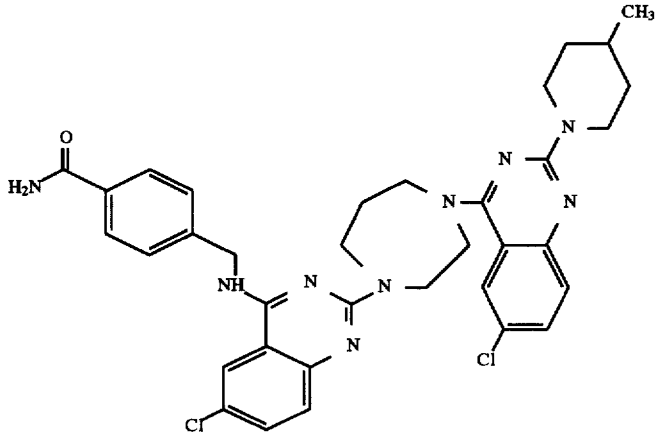 | |

TABLE 2-continued
| Ex.-No. | Structure | MS (ESI) |
|---|---|---|
| 56 | 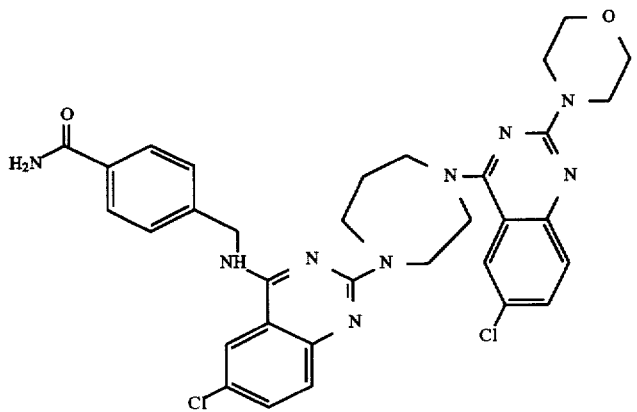 | |
| 57 | 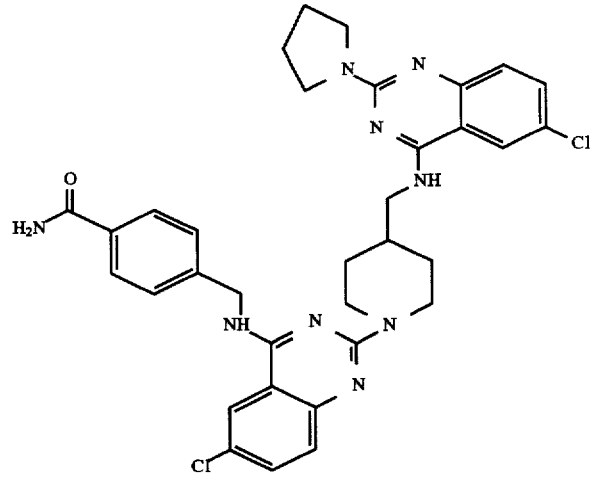 | |
| 58 | 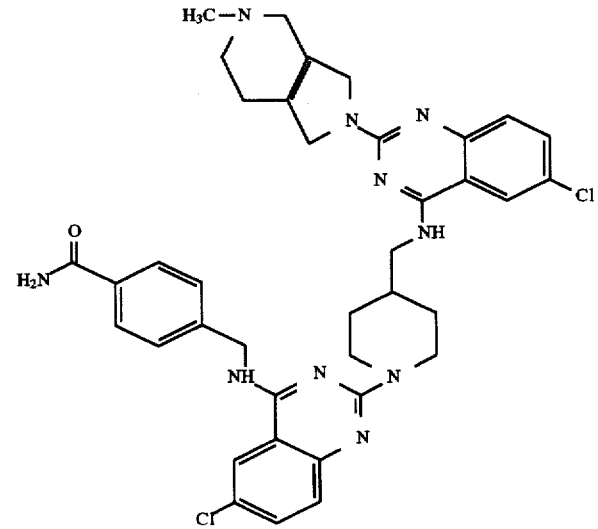 | |

TABLE 2-continued
| Ex.-No. | Structure | MS (ESI) |
|---|---|---|
| 59 | 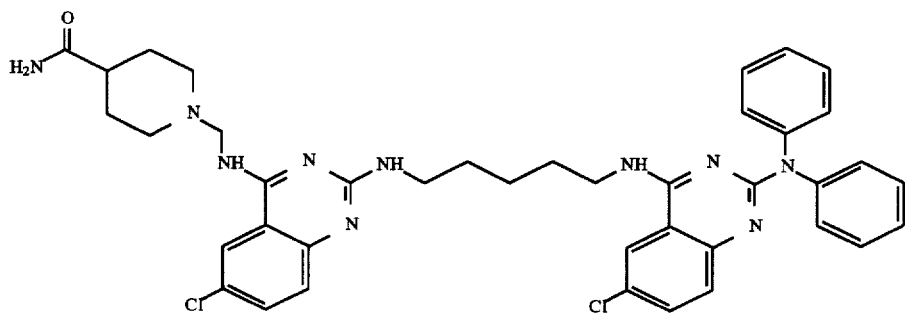 | |
| 60 | 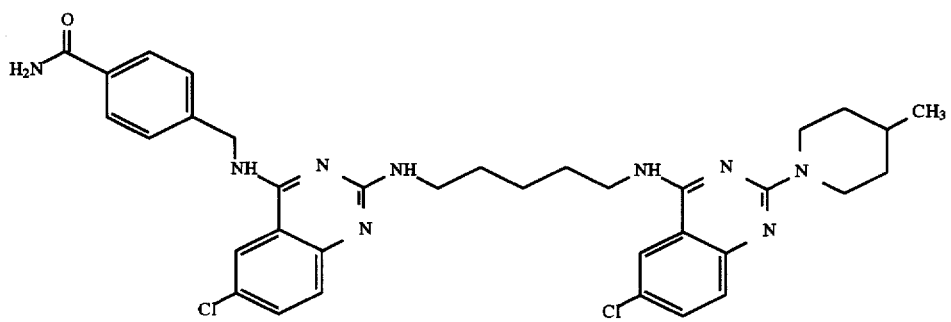 | |
| 61 | 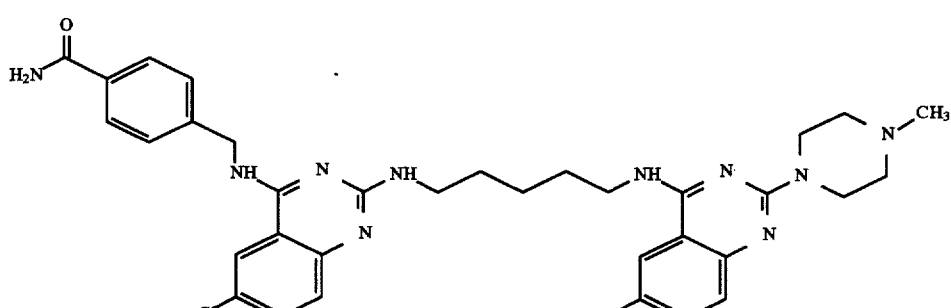 | |
| 62 | 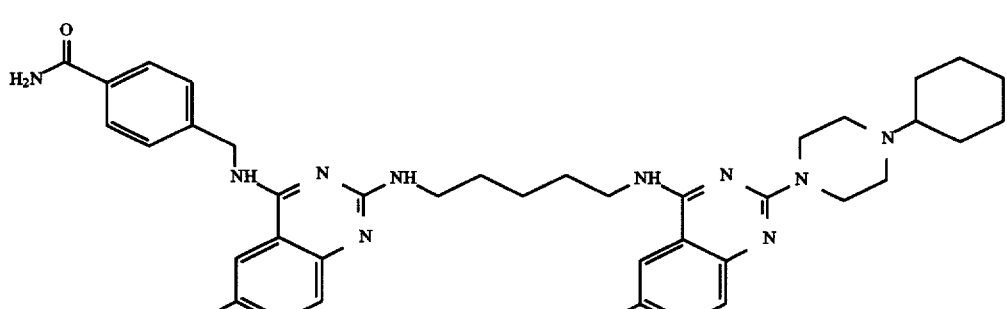 | |
| 63 | 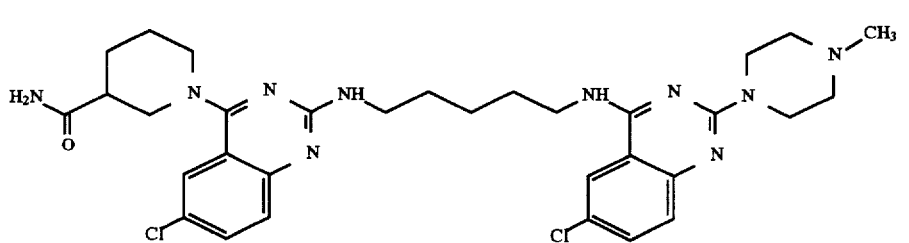 | |

TABLE 2-continued

| Ex.-No. | Structure | MS (ESI) |
|---|---|---|
| 64 | 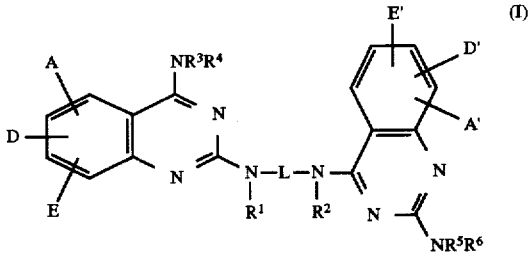 | |

EXAMPLE 65

4-(N'-(2-Diethylaminoquinazolin-4-yl)-aminomethyl)-N-(4-diethylaminoquinazolin-2-yl)-piperidine

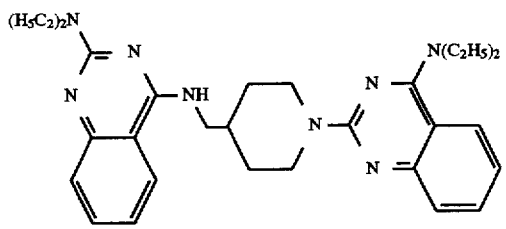

A mixture of the compound of Example III (500 mg, 1.8 mmol), 2-chloro-2-diethylaminoquinazoline (467 mg, 2.0 mmol) and Hünig's base (0.4 ml), 2.7 mmol) in 5 ml of butyronitrile was reacted for 12 hours at 120° C. After cooling, ethyl acetate (50 ml) and 50 ml of sodium hydroxide (10%) were added. The phases were separated and the aqueous phase was extracted with ethyl acetate (2×25 ml). The combined organic phases were dried (Na$_2$SO$_4$), concentrated on a rotary evaporator and purified by chromatography on silica gel (eluent: methylene chloride/ethanol/ammonia, 100/10/1) to give the free base as a solid.

M.p.: 82° C.
Yield: 354 mg (38%)

EXAMPLE 66

4-(N'-(4-Diethylaminoquinazolin-2-yl)-aminomethyl)-N-(2-diethylaminoquinazolin-4-yl)-piperidine

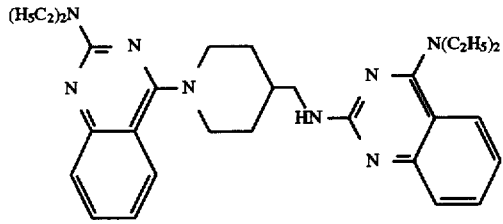

A mixture of the compound of Example III (500 mg, 1.8 mmol), 2-chloro-4-diethylaminoquinazoline (460 mg, 2.0 mol) and Hünig's base (0.47 ml, 2.7 mmol) in 5 ml of butyronitrile was reacted for 12 hours at 120° C. After cooling, ethyl acetate (50 ml) and 50 ml of sodium hydroxide (10%) were added. The phases were separated and the aqueous phase was extracted with ethyl acetate (2×25 ml). The combined organic phases were dried (Na$_2$SO$_4$), concentrated on a rotary evaporator and purified by chromatography on silica gel (eluent: methylene chloride/ethanol/ammonia, 100/10/1) to give the free base as a solid.

M.p.: 65° C.
Yield: 362 mg (45%)

We claim:
1. A compound of the formula:

(I)

in which

A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms, L is a linear or branched alkylene chain having up to 12 carbon atoms which is optionally interrupted by an oxygen or sulfur atom or by a group of the formula —NR$^7$, wherein R$^7$ is hydrogen or linear or branched alkyl having up to 4 carbon atoms, and where the alkylene chain is optionally substituted by up to 3 identical or different substituents selected from the group consisting of hydroxyl, linear or branched alkoxy having up to 5 carbon atoms, aryl or aralkoxy, each of which has up to 10 carbon atoms, and a 5- to 7-membered aromatic, optionally benzo-fused heterocycle having up to 3 heteroatoms selected from the group consisting of S, N and O, wherein said aryl or heterocycle rings are optionally substituted by halogen, hydroxyl, cyano, linear or branched alkoxy having up to 6 carbon atoms, or a radical of the formula —(NH)$_a$—CONR$^8$R$^9$, wherein R$^8$ and R$^9$ are identical or different and are hydrogen or linear or branched alkyl having up to 6 carbon atoms, and a is the number 0 or 1, or L is a radical of the formula —(CH$_2$)$_b$—T—(CH$_2$)$_c$, wherein b and c are identical or different and are the number 0, 1, 2, 3, 4 or 5, and T is cycloalkyl having 3 to 6 carbon atoms, aryl having 6 to 10 carbon atoms or a 3- to 8-membered, saturated or unsaturated, optionally benzo-fused and/or heterocyclically or carbocyclically bridged heterocycle having up to 3 heteroatoms selected from the group consisting of S, N and O, wherein said cycloalkyl, aryl and heterocycle rings are optionally substituted by up to 3 identical or different substituents selected from the group consisting of halogen, cyano, hydroxyl, nitro, carboxyl, linear or branched alkyl, alkoxycarbonyl or alkoxy, each of which has up to 9 carbon atoms, and a radical of the formula —CO—NR$^{10}$R$^{11}$, wherein R$^{10}$ and R$^{11}$ are identical or different, are as defined above for R$^8$ and R$^9$ and are identical thereto or different therefrom, R$^1$ and R$^2$ are identical or different and are hydrogen, phenyl or linear or branched alkyl having up to 6 carbon atoms which is optionally substituted by hydroxyl, halogen or a radical of the formula —(CO)$_d$NR$^{12}$R$^{13}$, wherein d is the number 0 or 1 and

R$^{12}$ and R$^{13}$ are identical or different, are as defined above for R$^8$ and R$^9$ and are identical thereto or different therefrom, or R$^1$, R$^2$ and L, together with the two nitrogen atoms, form a 5- to 8-membered, sainted, partially unsaturated or aromatic, optionally also benzo-fused heterocycle having up to 2 heteroatoms selected from the group consisting of O, S and N, wherein said heterocycle ring is optionally substituted via nitrogen atoms by hydroxyl, carboxyl, linear or branched acyl or alkoxycarbonyl, each of which has up to 6 carbon atoms, phenyl or linear or branched alkyl having up to 6 carbon atoms wherein said alkyl group is optionally substituted by hydroxyl, carboxyl, ureido, linear or branched alkoxy, acylamino or alkoxycarbonyl, each of which has up to 5 carbon atoms, or a group of the formula —(CO)$_e$NR$^{14}$R$^{15}$, wherein e is the number 0 or 1 and

R$^{14}$ and R$^{15}$ are identical or different, are as defined above for R$^8$ and R$^9$ and are identical thereto or different therefrom, and/or the heterocycle formed by R$^1$, R$^2$ and L is optionally substituted by a radical of the formula —(CO)$_f$—NR$^{16}$R$^{17}$, wherein f is as defined above for d and is identical thereto or different therefrom, and R$^{16}$ and R$^{17}$ are identical or different, are as defined above for R$^8$ and R$^9$ and are identical thereto or different therefrom, or, in the case where b is the number 0 and c is as defined above, or c is the number 0 and b is as defined above, T and R$^1$ or, respectively, T and R$^2$, in each case together with the nitrogen atom, form a 3- to 8-membered, optionally benzo-fused and/or heterocyclically or carbocyclically bridged, saturated heterocycle ring having up to 2 heteroatoms selected from the group consisting of S, N and O, and R$^3$, R$^4$, R$^5$ and R$^6$ are identical or different and are hydrogen, phenyl, benzyl or linear or branched alkyl having up to 8 carbon atoms, both the rings and the alkyl optionally being substituted by up to 3 identical or different substituents selected from the group consisting of carboxyl, phenyl, hydroxyl, halogen and a radical of the formula —(CO)$_g$—NR$^{18}$R$^{19}$, wherein g is the number 0 or 1 and

R$^{18}$ and R$^{19}$ are identical or different, are as defined above for R$^8$ and R$^9$ and are identical thereto or different therefrom, or R$^3$ and R$^4$ and/or R$^5$ and R$^6$, in each case together with the nitrogen atom, form a radical of the formula

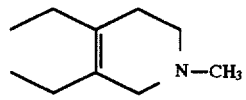

or R$^3$ and R$^4$ and/or R$^5$ and R$^6$ form a 5- and 7-membered saturated optionally substituted heterocycle ring which optionally contains a further heteroatom selected from the group consisting of S and O, or a radical of the formula —NR$^{20}$, wherein R$^{20}$ is hydrogen or a linear or branched alkyl chain having up to 6 carbon atoms which is optionally substituted by up to 3 identical or different substituents selected from hydroxyl, linear or branched alkoxy having up to 5 carbon atoms, halogen, cyano and a radical of the formula —(CO)$_h$NR$^{21}$R$^{22}$, wherein h is the number 0 or 1 and

R$^{21}$ and R$^{22}$ are identical or different and are hydrogen or linear or branched alkyl having up to 6 carbon atoms, or R$^{20}$ is cycloalkyl having 3 to 8 carbon atoms, phenyl or a radical of the formula

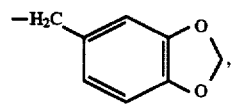

where optionally substituted heterocycle rings are optionally substituted by up to 3 identical or different substituents selected from the cycloalkyl having 3 to 6 carbon atoms, carboxyl, phenyl, linear or branched alkoxycarbonyl having up to 6 carbon atoms, and a group of the formula —CO—NR$^{23}$R$^{24}$, wherein R$^{23}$ and R$^{24}$ are identical or different, are as defined above for R$^8$ and R$^9$ and are identical thereto or different therefrom, and/or is optionally substituted by linear or branched alkyl having up to 6 carbon atoms which is optionally substituted by phenoxy, which in turn can be substituted by up to 3 identical or different halogens, and/or is optionally substituted by linear or branched alkoxy having up to 6 carbon atoms which in turn is optionally substituted by a 5- to 7-membered aromatic, optionally also benzo-fused heterocycle having up to 2 heteroatoms selected from the group consisting of S, N and O, or a salt thereof.

2. A compound according to claim 1
in which

A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 5 carbon atoms, L is a linear or branched alkylene chain having up to 10 carbon atoms which is optionally interrupted by an oxygen or sulfur atom or by a group of the formula $-NR^7$, wherein $R^7$ is hydrogen or linear or branched alkyl having up to 3 carbon atoms, and where the alkylene chain is optionally substituted by up to 2 identical or different substituents selected from hydroxyl, linear or branched alkoxy having up to 4 carbon atoms, phenyl, phenoxy, pyridyl and pyrimidinyl, wherein said phenyl, phenoxy, pyridyl and pyrimidinyl are optionally substituted by fluorine, chlorine, bromine, hydroxyl, cyano, linear or branched alkoxy having up to 5 carbon atoms, or a radical of the formula $-(NH)_a-CONR^8R^9$ wherein $R^8$ and $R^9$ are identical or different and are hydrogen or linear or branched alkyl having up to 5 carbon atoms, and a is the number 0 or 1, or L is a radical of the formula $-(CH_2)_b-T-(CH_2)_c$, wherein b and c are identical or different and are the number 0, 1, 2, 3 or 4, and T is cyclopropyl, cyclobutyl, cyclopentyl or cyclohexyl, phenyl, piperidinyl, pyridazinyl, pyridyl or thienyl wherein said groups are optionally substituted by up to 2 identical or different substituents selected from the fluorine, chlorine, bromine, hydroxyl, cyano, nitro, carboxyl, linear or branched alkyl, alkoxycarbonyl or alkoxy, each of which has up to 8 carbon atoms, and a radical of the formula $-CO-NR^{10}R^{11}$, wherein $R^{10}$ and $R^{11}$ are identical or different, are as defined above for $R^8$ and $R^9$ and are identical thereto or different therefrom.

$R^1$ and $R^2$ are identical or different and are hydrogen, phenyl or linear or branched alkyl having up to 5 carbon atoms which is optionally substituted by hydroxyl, fluorine, chlorine, bromine or a radical of the formula $-(CO)_dNR^{12}R^{13}$, wherein d is the number 0 or 1 and $R^{12}$ and $R^{13}$ are identical or different, are as defined above for $R^8$ and $R^9$ and are identical thereto or different therefrom, or $R^1$, $R^2$ and L, together with the two nitrogen atoms, form a piperazinyl, homopiperazinyl or diazabicyclooctanyl ring which is optionally substituted via a nitrogen group by hydroxyl, carboxyl, linear or branched acyl or alkoxycarbonyl, each of which has up to 5 carbon atoms, phenyl or linear or branched alkyl having up to 5 carbon atoms wherein said alkyl groups are optionally substituted by hydroxyl, carboxyl, ureido, linear or branched alkoxy, acylamino or alkoxycarbonyl, each of which has up to 4 carbon atoms, or a group of the formula $-(CO)_eNR^{14}R^{15}$ wherein e is the number 0 or 1 and and $R^{14}$ are identical or different, are as defined above for $R^8$ and $R^9$ and are identical thereto or different therefrom, and/or the piperazinyl, homopiperazinyl or diazabicyclooctanyl ring is optionally substituted by a radical of the formula $-(CO)_f-NR^{16}R^{17}$, wherein f is as defined above for d and is identical thereto or different therefrom, and $R^{16}$ and $R^{17}$ are identical or different, are as defined above for $R^8$ and $R^9$ and are identical thereto or different therefrom, or, in the case where b is the number 0 and c is as defined above, or c is the number 0 and b is as defined above, T and $R^1$ or, respectively, T and $R^2$, in each case together with the nitrogen atom, form a pyrrolidinyl or piperidinyl ring, and $R^3$, $R^4$, $R^5$ and $R^6$ are identical or different and are hydrogen, phenyl, benzyl or linear or branched alkyl having up to 7 carbon atoms, both the rings and the alkyl optionally being substituted by up to 2 identical or different substituents selected from carboxyl, phenyl, hydroxyl, fluorine, chlorine, bromine and a radical of the formula $-(CO)_gNR^{18}R^{19}$, wherein g is the number 0 or 1 and $R^{18}$ and $R^{19}$ are identical or different, are as defined above for $R^8$ and $R^9$ and are identical thereto or different therefrom, or $R^3$ and $R^4$ and/or $R^5$ and $R^6$, in each case together with the nitrogen atom, form an optionally substituted morpholine, optionally substituted pyrrolidine, optionally substituted piperidine or optionally substituted thiomorpholine ring or a radical of the formula

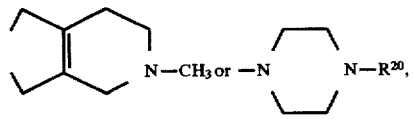

wherein $R^{20}$ is hydrogen or a linear or branched alkyl chain having up to 5 carbon atoms which is optionally substituted by up to 2 identical or different substituents selected from hydroxyl, linear or branched alkoxy having up to 4 carbon atoms, fluorine, chlorine, bromine, cyano and a radical of the formula —$(CO)_h NR^{21}R^{22}$, wherein h is the number 0 or 1 and $R^{21}$ and $R^{22}$ are identical or different and are hydrogen or linear or branched alkyl having up to 5 carbon atoms, or $R^{20}$ is cyclopropyl, cyclobutyl, cyclopentyl, cyclohexyl, phenyl or a radical of the formula

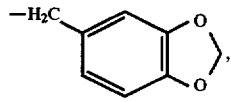

where the optionally substituted heterocyclic rings are optionally substituted by up to 2 identical or different substituents selected from the group consisting of cyclopropyl, cyclobutyl, cyclopentyl, cyclohexyl, carboxyl, phenyl, linear or branched alkyl or alkoxycarbonyl, each of which has up to 5 carbon atoms, and a group of the formula —$CO$—$NR^{23}R^{24}$, wherein $R^{23}$ and $R^{24}$ are identical or different, are as defined above for $R^8$ and $R^9$ and are identical thereto or different therefrom, and/or are optionally substituted by linear or branched alkyl having up to 5 carbon atoms which is optionally substituted by phenoxy, wherein said phenoxy group is optionally substituted by up to 2 identical or different substituents selected from fluorine, chlorine and bromine, and/or are optionally substituted by linear or branched alkoxy having up to 5 carbon atoms which is optionally substituted by morpholine, pyrrolidine, piperidine, thiomorpholine or piperazine ring, or a salt thereof.

3. A compound according to claim 1 in which

A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 3 carbon atoms, L is a linear or branched alkylene chain having up to 8 carbon atoms which is optionally interrupted by a group of the formula —$NR^7$, wherein $R^7$ is hydrogen, methyl or ethyl, and where the alkylene chain is optionally substituted by hydroxyl, linear or branched alkoxy having up to 3 carbon atoms, phenyl, phenoxy or pyridyl, wherein said phenyl, phenoxy or pyridyl rings are optionally substituted by fluorine, chlorine, bromine, hydroxyl, cyano, linear or branched alkoxy having up to 3 carbon atoms, or a radical of the formula —$(NH)_a$—$CONR^8R^9$, wherein $R^8$ and $R^9$ are identical or different and are hydrogen or linear or branched alkyl having up to 3 carbon atoms, and a is the number 0 or 1, or L is a radical of the formula —$(CH_2)_b$—T—$(CH_2)_c$, wherein b and c are identical or different and are the number 0, 1, 2 or 3, and T is cyclopropyl, cyclobutyl, cyclopentyl, cyclohexyl, phenyl, piperidinyl, pyridazinyl, pyridyl or thienyl wherein each of the groups are optionally substituted by up to 3 identical or different substituents selected from the group consisting of fluorine, chlorine, bromine, hydroxyl, cyano, nitro, carboxyl, linear or branched alkyl, alkoxycarbonyl or alkoxy, each of which has up to 6 carbon atoms, and a radical of the formula —$CO$—$NR^{10}R^{11}$, wherein $R^{10}$ and $R^{11}$ are identical or different, are as defined above for $R^8$ and $R^9$ and are identical thereto or different therefrom, $R^1$ and $R^2$ are identical or different and are hydrogen, phenyl or linear or branched alkyl having up to 4 carbon atoms which is optionally substituted by hydroxyl, fluorine, chlorine, bromine or a radical of the formula —$(CO)_d NR^{12}R^{13}$, wherein d is the number 0 or 1 and $R^{12}$ and $R^{13}$ are identical or different, are as defined above for $R^8$ and $R^9$ and are identical thereto or different therefrom, or $R^1$, $R^2$ and L, together with the two nitrogen atoms, form a piperazinyl, homopiperazinyl or diazabicyclooctanyl ring which is also optionally substituted via a nitrogen group by hydroxyl, carboxyl, linear or branched acyl or alkoxycarbonyl, each of which has up to 4 carbon atoms, phenyl or linear or branched alkyl having up to 3 carbon atoms wherein said alkyl groups are optionally substituted by hydroxyl, carboxyl, ureido, linear or branched alkoxy, acylamino or alkoxycarbonyl, each of which has up to 3 carbon atoms, or a group of the formula —$(CO)_e NR^{14}R^{15}$ wherein e is the number 0 or 1 and $R^{14}$ and $R^{15}$ are identical or different, are as defined above for $R^8$ and $R^9$ and are identical thereto or different therefrom, and/or the piperazinyl, homopiperazinyl or diazabicyclooctanyl ring is optionally substituted by a radical of the formula —$(CO)_f$—$NR^{16}R^{17}$, wherein f is as defined above for d and is identical thereto or different therefrom, and $R^{16}$ and $R^{17}$ are identical or different, are as defined above for $R^8$ and $R^9$ and are identical thereto or different therefrom, or, in the case where b is the number 0 and c is as defined above, or c is the number 0 and b is as defined above, T and $R^1$ or, respectively, T and $R^2$, in each case together with the nitrogen atom, form a pyrrolidinyl or piperidinyl ring, and $R^3$, $R^4$, $R^5$ and $R^6$ are identical and are hydrogen, phenyl, benzyl or linear or branched alkyl having up to 6 carbon atoms, both the phenyl and benzyl rings and the alkyl groups are optionally substituted by up 2 identical or different substituents selected from the carboxyl, phenyl, hydroxyl, fluorine, chlorine, bromine and a radical of the formula —(CO)$_g$NR$^{18}$R$^{19}$, wherein g is the number 0 or 1 and

R$^{18}$ and R$^{19}$ are identical or different, are as defined above for R$^8$ and R$^9$ and are identical thereto or different therefrom, or R$^3$ and R$^4$ and/or R$^5$ and R$^6$, in each case together with the nitrogen atom, form a morpholinyl, pyrrolidinyl or piperidinyl ring or a radical of the formula

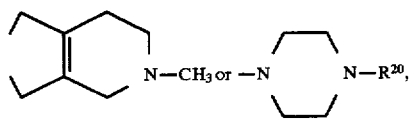

wherein

R$^{20}$ is hydrogen or a linear or branched alkyl chain having up to 8 carbon atoms which is optionally substituted by up to 2 identical or different substituents selected from the group consisting of hydroxyl, linear or branched alkoxy having up to 3 carbon atoms, fluorine, chlorine, bromine, cyano and a radical of the formula —(CO)$_h$NR$^{21}$R$^{22}$, wherein h is the number 0 or 1 and

R$^{21}$ and R$^{22}$ are identical or different and are hydrogen or linear or branched alkyl having up to 4 carbon atoms, or R$^{20}$ is cyclopropyl, cyclopentyl, cyclohexyl, phenyl or a radical of the formula

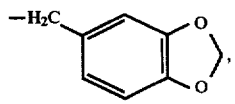

where the morpholinyl, pyrrolidinyl or piperidinyl rings listed above are optionally substituted by up to 2 identical or different substituents selected from the group consisting of cyclopropyl, cyclobutyl, cyclopentyl, cyclohexyl, carboxyl, phenyl, linear or branched alkyl or alkoxycarbonyl, each of which has up to 4 carbon atoms, and a group of the formula —CO—NR$^{23}$R$^{24}$, wherein R$^{23}$ and R$^{24}$ are identical or different, are as defined above for R$^8$ and R$^9$ and are identical thereto or different therefrom, and/or are optionally substituted by linear or branched alkyl having up to 4 carbon atoms which is optionally substituted by phenoxy, wherein said phenoxy group is optionally substituted by up to 3 identical or different substituents selected from fluorine, chlorine and bromine, and/or are optionally substituted by linear or branched alkoxy having up to 4 carbon atoms which is optionally substituted by morpholine, pyrrolidine, piperidine, thiomorpholine or piperazine ring, or a salt thereof.

4. A process for the preparation of the compounds according to claim 1, wherein (A) compounds of the general formula (II):

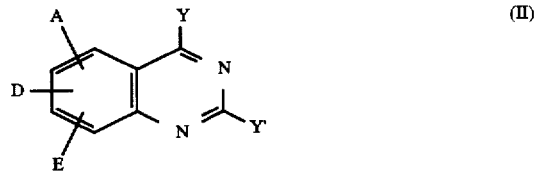

in which

A, D and E are as defined in claim 1 and

Y and Y' are identical or different and are fluorine or chlorine, are initially converted to the compounds of the general formula (IV):

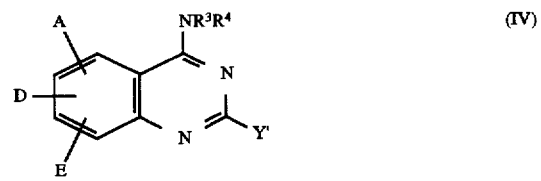

in which

A, D, E, Y', R$^3$ and R$^4$ are as defined in claim 1, by reaction with amines of the general formula (III):

HNR$^3$R$^4$     (III)

in which

R$^3$ and R$^4$ are as defined in claim 1, in inert solvents, optionally in the presence of a base and/or an auxiliary, said compounds of the formula (IV) are reacted with amines of the general formula (V):

in which

R$^1$, R$^2$ and L are as defined in claim 1, in inert solvents, optionally in the presence of a base and/or an auxiliary, to give the compounds of the general formula (VI):

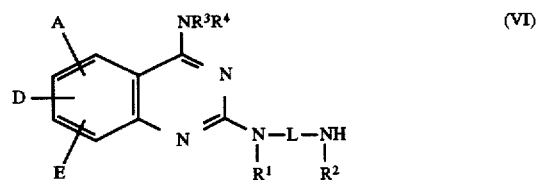

in which

A, D, E, L, R$^1$, R$^2$, R$^3$ and R$^4$ are as defined in claim 1, said compounds of the formula (VI) are then reacted with compounds of the general formula (IIa):

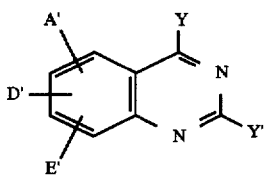

in which

A', D' and E' are as defined in claim 1, and

Y and Y' are identical or different and are as defined in claim 1, in inert solvents, optionally in the presence of a base, to give the compounds of the general formula (VII):

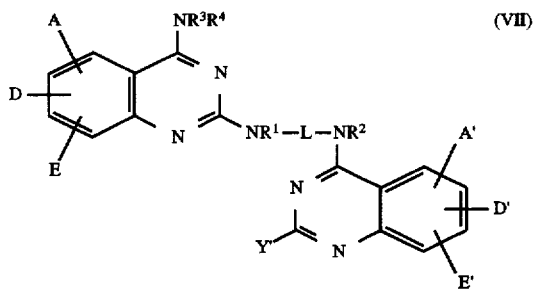

in which

A, A', D, D', E, E', $R^1$, $R^2$, $R^3$, $R^4$, L and Y are as defined above, and, in a last step, said compounds of the formula (VII) are reacted with amines of the general formula (VIII):

$HNR^5R^6$ (VIII)

in which $R^5$ and $R^6$ are as defined in claim 1, or (B) compounds of the general formula (VI) are reacted with compounds of the general formula (IX):

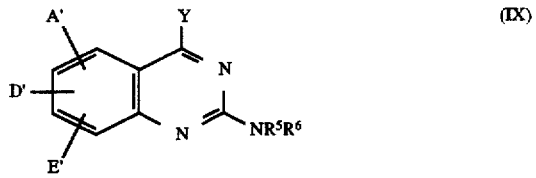

in which

A', D', E', Y, $R^5$ and $R^6$ are as defined in claim 1, in inert solvents, optionally in the presence of a base and/or an auxiliary, or (C) the synthesis steps indicated under are carried out on a solid phase, binding to the resin being effectived via the substituent radical —$NR^3R^4$ and, when the synthesis had ended, cleaving the resin.

5. A pharmaceutical composition which comprises an effective remount of a compound according to claim 1.

6. A method of treating diseases affected by binding to the apamine-sensitive potassium channels which comprises administering an effective amount of a compound according to claim 1 to a host in need thereof.

7. A method according to claim 6, wherein the disease state is depression.

* * * * *

UNITED STATES PATENT AND TRADEMARK OFFICE
CERTIFICATE OF CORRECTION

PATENT NO. : 5,739,127
DATED : April 14, 1998
INVENTOR(S) : Schohe-Loop, et al.

It is certified that error appears in the above-indentified patent and that said Letters Patent is hereby corrected as shown below:

| | |
|---|---|
| Col. 57, line 39 | After " membered " delete " sainted " and substitute -- saturated -- |
| Col. 59, line 14 | Before " A' " insert -- A, -- |
| Col. 60, line 15 | Delete " $-(CO)_6 NR^{14}R^{15}$ " and substitute -- $(CO)_e NR^{14}R^{15}$ -- |
| Col. 60, line 19 | Before " $R^{14}$ " delete " and ", after " $R^{14}$ " insert -- and $R^{15}$ -- |
| Col. 66, line 21 | After " under " insert [A] -- |

Signed and Sealed this

First Day of June, 1999

Q. TODD DICKINSON

Attest:

Attesting Officer

Acting Commissioner of Patents and Trademarks